US008540761B2

(12) United States Patent
Rabkin et al.

(10) Patent No.: US 8,540,761 B2
(45) Date of Patent: Sep. 24, 2013

(54) TEMPORARY, REPOSITIONABLE OR RETRIEVABLE INTRALUMINAL DEVICES

(75) Inventors: Dmitry J. Rabkin, Framingham, MA (US); Eval Morag, East Hampton, MA (US); Ophir Perelson, Beverly Hills, CA (US)

(73) Assignee: Intek Technology LLC, Wilmington, DE (US)

( * ) Notice: Subject to any disclaimer, the term of this patent is extended or adjusted under 35 U.S.C. 154(b) by 569 days.

(21) Appl. No.: 12/573,525

(22) Filed: Oct. 5, 2009

(65) Prior Publication Data

US 2010/0087913 A1    Apr. 8, 2010

Related U.S. Application Data

(63) Continuation of application No. 10/333,599, filed as application No. PCT/US02/38374 on Dec. 3, 2002, now abandoned.

(60) Provisional application No. 60/337,060, filed on Dec. 3, 2001.

(51) Int. Cl.
*A61F 2/82* (2006.01)
(52) U.S. Cl.
USPC .......................... 623/1.15; 623/1.16; 623/1.19
(58) Field of Classification Search
USPC ........................................ 623/1.15, 1.16, 1.19
See application file for complete search history.

(56) References Cited

U.S. PATENT DOCUMENTS

| 5,037,427 | A | * | 8/1991 | Harada et al. ............... 606/108 |
| 5,593,442 | A | | 1/1997 | Klein |
| 5,688,418 | A | | 11/1997 | Yoshiyasu et al. |
| 6,042,606 | A | | 3/2000 | Frantzen |
| 6,296,661 | B1 | | 10/2001 | Davila et al. |
| 6,447,478 | B1 | * | 9/2002 | Maynard ................... 604/95.05 |
| 6,524,335 | B1 | * | 2/2003 | Hartley et al. .............. 623/1.13 |
| 6,656,215 | B1 | * | 12/2003 | Yanez et al. ............... 623/1.13 |
| 6,790,218 | B2 | * | 9/2004 | Jayaraman ................. 606/191 |
| 2001/0011188 | A1 | | 8/2001 | Berry et al. |

FOREIGN PATENT DOCUMENTS

| EP | 1036550 | | 9/2000 |
| EP | 1138280 | | 1/2004 |
| EP | 1294318 | | 12/2004 |
| FR | 2745172 | A1 * | 8/1997 |
| GB | 2360456 | | 9/2001 |
| WO | 9531945 | | 5/1995 |

OTHER PUBLICATIONS

Search Report dated Jan. 11, 2005 (5 pages).

* cited by examiner

*Primary Examiner* — David H Willse
*Assistant Examiner* — Javier Blanco
(74) *Attorney, Agent, or Firm* — Cozen O'Connor

(57) ABSTRACT

A stent formed of a metallic material having a two-way memory adapted to be retrieved or repositioned after delivery includes an elongated tubular body and at least one crown connected to a respective longitudinal end of the body, the crown including a plurality of unconnected leaves, each leaf having a longitudinally extending frame connected at one end to the end of the body. A method of manufacturing the stent so that the crown has a greater two-way memory effect than the body is disclosed.

25 Claims, 18 Drawing Sheets

TEMPORARY, REPOSITIONABLE OR RETRIEVABLE INTRALUMINAL DEVICES

This application is a continuation of application Ser. No. 10/333,599 filed Jan. 21, 2003 which is a national stage of PCT/US 2002/8374 filed under 35 U.S.C. § 371 on Dec. 3, 2002, which claims priority from provisional patent application Ser. No. 60/337,060 filed Dec. 3, 2001.

FIELD OF THE INVENTION

The present invention generally relates to advanced medical endoluminal devices for, and methods of, minimally invasive treatment of blockages of the blood vessels and other tubular organs. More particularly, the present invention relates to self-expanding stents for internal reinforcing of diseased tubular structure and/or for local delivery of pharmacological or radioactive agents having a beneficial advantage of repositioning or retrieval.

BACKGROUND OF THE INVENTION

A stent is a generally longitudinal cylindrical device formed of biocompatible material, such as a metal or plastic, which is used in the treatment of stenosis, strictures, or aneurysms in body blood vessels and other tubular body structures, such as the esophagus, bile ducts, urinary tract, intestines or tracheo-bronchial tree. References hereafter to "blood vessels" and "vessels" will be understood to refer to all such tubular body structures. A stent is held in a reduced diameter state during its passage through a low profile catheter until delivered to the desired location in the blood vessel, whereupon the stent radially expands to an expanded diameter state in the larger diameter vessel to hold the vessel open. As discussed below, radial expansion of the stent may be accomplished by an inflatable balloon attached to a catheter, or the stent may be of the self-expanding type that will radially expand once deployed from the end portion of a delivery catheter.

Stented vessels have a tendency to develop aggressive intimal hyperplasia. Intimal hyperplasia is part of the endothelialization process by which the stent becomes incorporated into the vessel wall as a result of the vessel's reaction to a foreign body, and is characterized by deposition of cell layers covering the stent. It eventually results in formation of a neointima, which coats the stent and buries it completely in the vessel wall.

Endothelialization generally improves patency rates and the more complete the apposition of the stent to the vessel wall, the more uniform and optimal is the degree of endothelialization. Of course, a fundamental concern is that the stent be deployed in the correct desired location in the vessel as precisely as possible in the first place. This is important when delivering radiation or medication to a particular location using the stent.

Stents fall into one of two categories based on their mechanism of deployment and radial expansion, namely, balloon-expandable stents and self-expanding stents.

Balloon-expandable stents (BES) are mounted in their reduced diameter state on nylon or polyethylene balloons, usually by manual crimping, while others are available pre-mounted. One example of a BES is shown in U.S. Pat. No. 4,733,665 to Palmaz. BES rely solely on balloon dilation to attain the desired expanded configuration or state. This enables BES to be deployed in a relatively controlled gradual manner. BES in general have more strength than self-expanding stents and initially resist deformation as well as recoil. BES behave elastically but eventually yield and become irreversibly, i.e. plastically, deformed under external force. Most BES are less flexible than self-expanding stents and are therefore less capable of being delivered through tortuous vessels and, when a BES is deployed in a tortuous vessel, it often straightens the vessel, forcing the vessel to conform to the shape of the stent rather than vice versa. This generally results in portions of the stent not being completely apposed to the vessel wall which in turn affects endothelialization and overall patency rate.

On the other hand, BES can generally be deployed in a relatively precise manner at the correct desired location in the vessel since they can be deployed in a controlled gradual manner by gradually controlling the inflation of the balloon. This ability to gradually control the expansion of the stent, along with the fact that BES rarely change their position on the balloon during inflation, enable fine adjustments to be made by the operator in the position of the stent within the vessel prior to stent deployment.

Self-expanding stents (SES) are formed of braided stainless steel wire or shape-memory alloy such as nitinol and are generally delivered to desired locations in the body in a reduced diameter state in a low profile catheter while covered by an outer sheath which partially insulates the SES from body temperature and mechanically restrains them.

Nitinol is an alloy comprised of approximately 50% nickel and 50% titanium. Nitinol has properties of superelasticity and shape memory. Superelasticity refers to the enhanced ability of material to be deformed without irreversible change in shape. Shape memory is the ability of a material to regain its shape after deformation at a lower temperature. These physical properties of nitinol allow complex device configurations and high expansion ratios enabling percutaneous delivery through low profile access systems.

Superelasticity and shape memory are based on nitinol's ability to exist in two distinctly different, reversible crystal phases in its solid state at clinically useful temperatures. The alignment of crystals at the higher temperature is called the austenite (A) phase; the alignment of crystals at the lower temperature is called the martensite (M) phase. In between is a temperature interval of gradual transition between the A and M phases.

Under external force, the shape of a nitinol device can be greatly deformed without irreversible damage. Depending on the temperature at which this external force is applied, superelastic or shape memory effects prevail. In close vicinity to or above the temperature defining transition into the full A state, superelasticity results: as soon as the deforming force is released, the device immediately assumes it original shape. When nitinol is deformed at or below the lower temperature of the complete M transition, the shape memory effect can be exploited. The device retains its deformed shape even after the external force is removed as long as the temperature of the environment stays below the temperature of transition into A phase. Only during heating does the device resume its original shape.

While the shape memory effect is essentially a one-way type phenomena in which shape recovery occurs only upon heating the alloy to a temperature defining transition to the full A phase, by subjecting the alloy itself to a biasing force, i.e. an internal stress formed by dislocations introduced by plastic deformation in the alloy, a two-way shape memory can be imparted to the alloy so that cooling the alloy will induce a shape change.

One type of self-expanding stent is constructed of wire formed of a shape-memory alloy, such as nitinol, having a transition temperature of about body temperature, i.e. 37° C.

For example, reference is made to U.S. Pat. No. 5,746,765 to Kleshinski et al. The one-way transition temperature is the temperature of transformation of a nitinol device from its collapsed state into a fully expanded configuration. The stent is pre-loaded on a low profile catheter by crimping the stent at room temperature (at which it can be plastically deformed) onto the catheter. An outer sheath covers the crimped stent and at least partially thermally insulates the stent as it is delivered to the desired location. Upon reaching the desired location, the sheath is withdrawn and the stent is exposed to body temperature whereupon it is naturally warmed to body temperature and expands to its expanded diameter state in supporting contact with the vessel wall. In a fully expanded state within the human body, the stent is capable of exerting considerable radial force on the surrounding structures, which allows mechanical opening of the vessel lumen and maintaining its long-term patentcy for free passage of flow.

If an alloy is used for which shape recovery occurs above body temperature, the SES must be heated after release into the body. If shape recovery occurs below body temperature, the device may be cooled during the delivery to prevent expansion inside the delivery catheter. If shape recovery occurs at body temperature, no heating or cooling is necessary during the delivery and deployment, provided delivery is relatively speedy. If, however, a tortuous iliac anatomy or other interference delays prompt deployment of a nitinol stent with these characteristics, premature warming to body temperature could cause expansion in the delivery sheath, increase friction, and interfere with delivery. In this instance, flushing with a cool solution has been suggested.

SES do not require any special preparation prior to deployment. SES behave elastically throughout their lifetime, and do not become irreversibly deformed. When deployed, the nominal diameter is purposely selected to be greater that the diameter of the vessel. Therefore, once deployed, an SES exerts continuous outward force on the vessel as it tries to expand to its original dimensions. The ability of an SES to continuously exert an outward force on the vessel coupled with the greater flexibility of SES, generally results in optimal wall apposition, thereby optimizing endothelialization and improving patency rates. Nitinol self-expanding stents have been designed having good radial and hoop strength.

However, while SES are preferable relative to BES in many applications with respect to achieving optimized endothelialization and increased patency rates, currently available arrangements of SES are not entirely satisfactory. It has generally not been possible to deploy SES in the correct desired location in a vessel as precisely as in the case of BES with currently available delivery arrangements for the reason that the temperature of the SES rapidly increases to body temperature upon withdrawal of the outer sheath and therefore the stent quickly expands into engagement with the vessel wall. Consequently, there is not always enough time to finely adjust the position of the SES as it quickly expands, and it is not uncommon for the distal end of an SES, which is exposed to body temperature first, and which therefore expands before the rest of the SES, to engage and become attached to the vessel wall in the wrong position and in turn inhibit or prevent further adjustments in the position of the SES in the vessel.

Still another drawback in conventional arrangements for delivering and deploying SES is the possibility that when delivery is protracted, the SES is exposed to body temperature inside the delivery system. The deployment process can then become more difficult—the device may open abruptly after being freed from the system and may "jump" beyond the target as the SES expands during deployment. BES cannot be repositioned or retrieved after deployment and while arrangements have been proposed for enabling the repositioning and/or retrieval of SES formed of two-way shape memory material, no practical workable arrangement has been developed.

A malpositioned stent often requires an additional stent placement to correct the mistake and achieve the desired results. The stents will remain in the vessel for the entire life of the patient. In a high percentage of patients, the stent will become the site of recurrent stenosis due to an aggressive neointimal proliferation. These patients require repeated interventions, which often include balloon angioplasty and/or additional stent placement.

The most striking illustration of these problems is seen in cardiac patients. Stents and balloon angioplasty transformed the care of patients with heart disease. Each year, about 700,000 patients in the U.S. undergo angioplasty, in which a balloon is used to clear an obstruction in a coronary artery and a stent is deployed to keep it open. Yet a disturbingly high 15% to 20% of the procedures fail within six months, due to the aggressive neointimal proliferation. These patients will often undergo further major treatments, which might be repeated several times.

The need to be able to reposition and/or retrieve stents from a vessel also arises from the fact that a new generation of stents has been developed, that not only prop open the vessel, but which deliver drugs to the site of the blockage in an effort to minimize or eliminate neointimal proliferation and keep the vessel open for long periods of time. Studies have shown that stents coated with a drug called rapamycin, essentially eliminate re-stenosis. Other medications, such as nitric oxide and paclitaxel or similar compounds, also have a potential to prevent proliferation of scar tissue by killing such cells. One concern is whether the drugs might work too well, inhibiting not only re-stenosis, but also the necessary growth of the thin layer of neointima. As previously described, this thin layer of cells, which grows over the stent, smoothes its surface (similar to a layer of Teflon), so blood cells can flow over it without damaging themselves. A damaged blood cell initiates a chemical cascade, which results in clot formation. Therefore an exposed bare metallic stent carries a risk of inducing thrombus formation within it.

The potential of radioactive stents to prevent re-stenosis is an additional area of active development, since local radiation has been shown to inhibit the growth of neointima and halt the progression of atherosclerotic disease.

One can therefore appreciate the benefit of being able to retrieve a stent used for local drug delivery or radiation treatment, after it has achieved its desired effect. This would eliminate potential risk of thrombus formation at the site of the exposed bare stent.

In summary, ideally an optimal stent should possess and combine all the positive traits mentioned so far in each of the stent categories. The stent should be pre-loaded on the delivery apparatus and should not require special preparation. It should be flexible to enhance apposition to the vessel wall. It should provide a controlled gradual deployment without stent migration to ensure deployment of the stent in the correct location. Lastly, in case of a malpositioned stent, or stent which is deployed for the purpose of its temporary effect, such as for local drug delivery, the stent should have the option of enabling repositioning and/or retrieval.

SES can be preloaded on the delivery apparatus, do not require special preparation and are flexible. However, to date, no satisfactory system is available for repositioning and/or retrieving a SES. While arrangements have been suggested in the prior art for repositioning and retrieving SES formed of two-way shape memory material, these prior art arrangements all have drawbacks and have not been adopted in practice.

An arrangement for delivering, repositioning and/or retrieving an SES formed of a two-way shape memory alloy capable of expansion or collapsing in the radial direction in accordance with changes in temperature is disclosed in U.S. Pat. No. 5,037,427 to Harada et al. According to Harada et al., a stent is made of nitinol alloy trained to have two-way shape memory. The stent is in an expanded diameter state at about body temperature and in a reduced diameter state at a temperature below body temperature. In delivering the stent, the stent is mounted in the reduced diameter state at the distal end of a catheter over a portion of the catheter having a number of side ports. Cooling water supplied through the catheter flows out from the side hole and is brought into contact with the stent during delivery to maintain the stent below body temperature and therefore in the reduced diameter state. When the SES is positioned at the desired location, the supply of the cooling water is stopped and the stent is warmed by the heat of the body and expands into supporting engagement with the wall of the vessel. The catheter is then withdrawn. In retrieving an already-positioned SES using this system, the distal end portion of the catheter is inserted into the expanded stent lumen and a cooling fluid is introduced into the catheter and discharged through the side ports at the distal end region into the vessel whereupon the stent is cooled and purportedly collapses onto the distal end portion of the catheter. The stent is retrieved by withdrawing the catheter. The patent suggests that the position of the stent can also be changed using this technique.

U.S. Pat. No. 5,746,765 to Kleshinski, Simon, and Rabkin also discloses a stent made from an alloy with two-way shape memory, which expands inside the vessel due to natural heating to body temperature. The stent is covered with an elastic sleeve. When the metal frame is softened by decreased temperature, the sleeve overcomes its radial force and promotes its further contraction for easier retrieval.

However, in both the arrangements disclosed in Harada et al. and Kleshinski et al., a substantial amount of very cold solution must be infused into the vessel in order to reduce the local temperature of the environment surrounding the stent. Cold temperature around the stent must be maintained for some time until the stent is delivered or recovered for retrieval or repositioning. This technique appears to be clinically impractical and not safe due to high risk of potential tissue and blood cell damage.

U.S. Pat. No. 6,077,298 to Tu et al. discloses a retractable stent made from a one-way shape-memory alloy, such as nitinol, that can be deployed into the body by means of dilation with a balloon catheter. For the stent retrieval, a radio frequency current within the range of 50 to 2,000 kHz must be applied directly to the stent to provide partial collapse of the stent after it is heated to a temperature above 43° C. to 90° C. However, if the transition temperature of the stent material is in the range of 43° C.-90° C., the radial force of the device will be greatly reduced at the body temperature of 37° C., and may not be sufficient for therapeutic effect. Heating of the stent to almost a boiling temperature can cause irreversible damage to vascular wall and blood coagulation.

U.S. Pat. No. 5,961,547 to Razavi, U.S. Pat. No. 5,716,410 to Wang et al., U.S. Pat. No. 5,449,372 to Schwaltz et al. and U.S. Pat. No. 5,411,549 to Peters disclose temporary or retractable stents in the shape of a spiral coil or a double helix. Although these stents are made of different materials, such as metal or plastic, and have differences in the techniques of their deployment (heat-activated, self-expanding or balloon expandable), as well as methods of their retrieval (mechanical straightening vs. softening by increasing temperature vs. latch retraction), all of them have one common feature. The stents are connected with a wire extending outside the patient at all times and when they have to be removed, they are simply retracted back into the catheter with or without prior softening of the material. For this reason these stents cannot be left in the human body for more than a couple of days. The connecting wire can traverse the entire body if the stent is placed in the coronary or carotid artery from the femoral approach, increasing risk of thrombus formation around the wire and distal embolization, thrombosis of the femoral artery and infection of the inquinal region.

U.S. Pat. No. 5,941,895 to Myler et al. discloses a removable cardiovascular stent with engagement hooks extending perpendicular to the axis of the stent into the vessel lumen. The stent retrieval technique requires introduction of an extraction catheter, which is adapted to grasp the engagement hooks of the stent with subsequent stent elongation in axial direction and reduction of its cross-sectional diameter. However, the stent with inwardly extending engagement members will likely require a larger delivery system than regular tubular devices. Any manipulation of the catheters and guidewires in the stented area may potentially accidentally engage the hooks of the stent with its subsequent dislodgment and damage of, the vessel. The hooks extending into the vessel lumen will cause turbulence of blood flow around them, leading to activation of the coagulation system and thrombus formation.

U.S. Pat. No. 5,833,707 to McIntyre et al. discloses a stent formed from a thin sheet of metal that has been wound around itself into a general cylindrical tight roll and expands inside the body by heating to body temperature. This stent is designed for predominant use in the human urethra and is not suitable for cardiovascular applications due to very large metal surface that could be thrombogenic and increased size of the delivery system. The stent can be removed from the body with the help of a cannula or pincer grips for grasping the edge of the stent. By rotating the pinched stent, the pincer or cannula cause the stent to telescopically coil into smaller diameter, which can then be retrieved from the urethra. This technique could be too traumatic for cardiovascular applications. The recovery apparatus will likely have a large profile, making this method not practical or feasible for percutaneous use in blood vessels or other tubular organs.

U.S. Pat. No. 5,562,641 to Flomenblit et al. discloses a spiral or cylindrical stent made from alloy with two-way shape memory capabilities. The stent expands inside the body by heating to the temperature of 50° C. to 80° C. with an electric current, injection of hot fluid, external radio frequency irradiation or use of radio frequency antenna inside the catheter. The stent can be removed from the body after cooling to a temperature, ranging from −10° C. to +20° C., at which the stent partially collapses in diameter and can be grasped with a catheter for retrieval. As discussed above, heating of the stent to a temperature over 80° C. could be unsafe, especially with intravascular injection of hot fluid. Use of external radio frequency irradiation will cause heating not only of the stent, but all tissues from the skin surface to the stented vessel deep inside the body and beyond. Cooling the stent to below the freezing temperature by injection of a very cold fluid into a blood circulation for removal is also impractical and not feasible in a real clinical setting.

SUMMARY OF THE INVENTION

Accordingly, it is an object of the present invention to provide a new and improved stent device for reinforcing blood vessels and other tubular body structures, that can be used temporarily to keep the vessels open.

Another object of the present invention is to provide a new and improved stent device, that can be repositioned after complete deployment using endovascular techniques.

Still another object of the present invention is to provide a new and improved stent device, that can be removed from the body completely after being implanted for a certain period of time using endovascular techniques.

Briefly, in accordance with one aspect of the present invention, these and other objects are attained by providing a specially constructed self-expanding stent formed of a shape memory alloy, such as Nitinol, which exhibits or is trained to have a second way memory, and can be partially or completely collapsed from its fully expanded condition by means of engaging with a thermal transfer device coupled to a catheter assembly. The stent has a configuration designed to interact with a retrieval device coupled to the catheter assembly which captures and holds the stent during repositioning and/or retrieval.

Thermal transfer devices and retrieval devices are preferably of the type disclosed in applicants' pending applications: Ser. Nos. 09/845,090 and 09/845,098, both filed Apr. 27, 2001 and assigned to the assignee of the instant application. The disclosures of these applications (hereinafter, the "prior applications") are incorporated herein in their entirety.

The thermal transfer device disclosed in the prior applications is constructed such that the temperature of the stent can be controlled quickly, precisely and non-invasively. Specifically, the temperature of the stent can be changed quickly by placing it in local heat transfer relationship with a thermal transfer device attached to the end of a catheter assembly. For present purposes, "local heat transfer relationship" means either the stent contacts the thermal device or the stent and thermal transfer device are sufficiently close, so that heat is transferred between the stent and the thermal transfer device without materially affecting the temperature of the surrounding tissue. The stent's temperature can be controlled relatively precisely since the stent has a low mass so that the temperature of the stent will essentially correspond to the temperature of the thermal transfer device, which has a much higher mass. Moreover, no liquid or gas will be infused into the vessel during the entire procedure.

This feature makes the arrangement particularly adapted for repositioning and/or retrieving stents formed of two-way shape memory alloys that have already been deployed in a vessel, such as in the repositioning of a misplaced stent, removal of a stent placed for temporary indications, or the removal of a stent that has completed the delivery of medication or radiation to a particular area. Specifically, for removal and/or repositioning of the stent, the thermal transfer device is structured and arranged to be initially positioned in the lumen of the already deployed stent in a collapsed condition, out of contact or other local heat transfer relationship with the deployed stent, and then expanded into contact, or other local heat transfer relationship with the stent. The temperature of the heat transfer device is adjusted so that the temperature of the deployed stent is reduced to that at which the stent obtains a relaxed, flexible state whereupon it separates from the vessel wall. The stent can then be engaged by capturing hooks attached to the catheter assembly and drawn into the catheter assembly and either removed from the body or repositioned using the initial delivery process described above.

The stent is constructed such that it is easily engaged by the capturing hooks forming part of the retrieval device coupled to the catheter assembly for purposes of retrieval and/or repositioning. This arrangement prevents the stent from being carried away by the bloodstream or from migrating on the catheter. The retrieval device is also structured and arranged to assist in drawing the stent in its flexible and pliable condition into the catheter assembly for repositioning and retrieval.

One advantageous aspect of the present invention is that the stent is formed of two main components, namely, a stent body and a specially constructed stent crown provided at one or both ends of the stent body. The crown is preferably imparted with a greater two-way memory than the rest of the stent. The two-way shape memory and construction of the crown facilitate repositioning and/or removal of the stent. The actual repositioning and/or retrieval, can be performed immediately after stent deployment, during the same procedure or weeks later, depending on the clinical situation, the exact purpose of the stent and its applications.

Another advantageous aspect of the present invention is the particular geometry of the annular rings defining each respective functional segment of the stent, with or without the crown, and the relative strength of the two-way memory imparted to that segment to provide advantageous flexibility, radial force and two-way memory effect for each segment to thereby provide a stent which is not difficult to position, which is effective in operation, and which can be repositioned and/or retrieved using the techniques disclosed in the prior applications.

DESCRIPTION OF THE DRAWINGS

A more complete appreciation of the present invention and many of the attendant advantages thereof will be readily understood by reference to the following detailed description when considered in connection with the accompanying drawings in which.

DESCRIPTION OF THE PREFERRED EMBODIMENTS

Except where noted, stents to be retrieved and/or repositioned in accordance with the invention are formed of a shape memory material, as Nitinol, having or trained to have a second cold memory, i.e. a two-way shape memory material. When released into the vessel or other tubular structure and naturally warmed to first transition temperature at or below body temperature of 37° C., the stent expands and recovers its previously imprinted intended functional shape at or below body temperature. In a fully expanded state within the human body, the stent is capable of exerting considerable radial force on the surrounding structures, which allows mechanical opening of the vessel lumen and maintaining its long-term patency for free passage of flow. When the fully expanded stent is cooled to a temperature in the range of −10° C. to +35° C., it becomes compliant, has a reduced stress state, and can be compressed into a reduced diameter, small enough to fit within a low profile delivery system for percutaneous retrieval and repositioning.

Stents according to the invention can be constructed of a single continuous thermal shape memory wire, or cut from a tube with laser technology, or formed with a photoetching technique from thermal shape memory tubing to create a mesh-like configuration.

Figure 1:
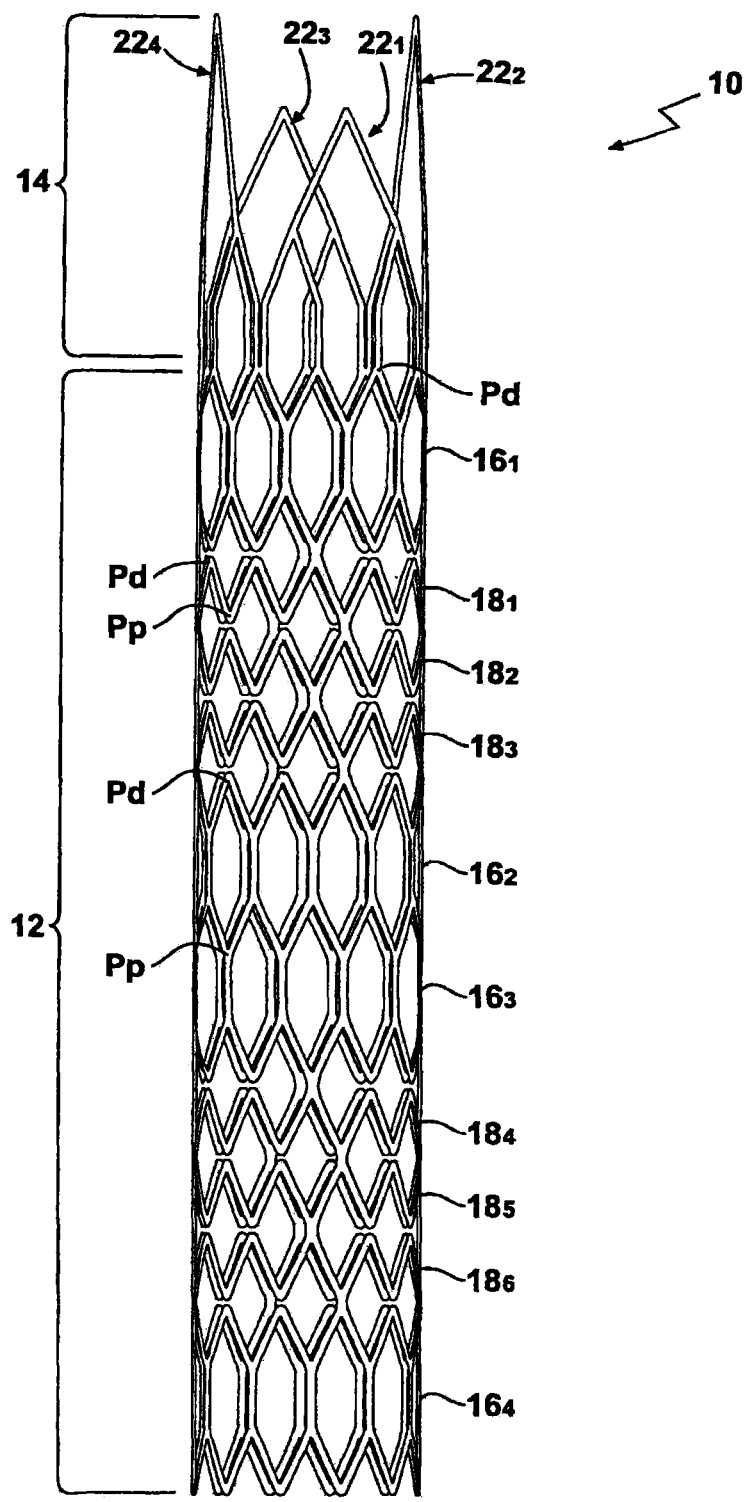
FIG. 1 is a front elevation view of one embodiment of a retrievable/repositionable stent according to the invention shown in its expanded configuration.
Figure 2:
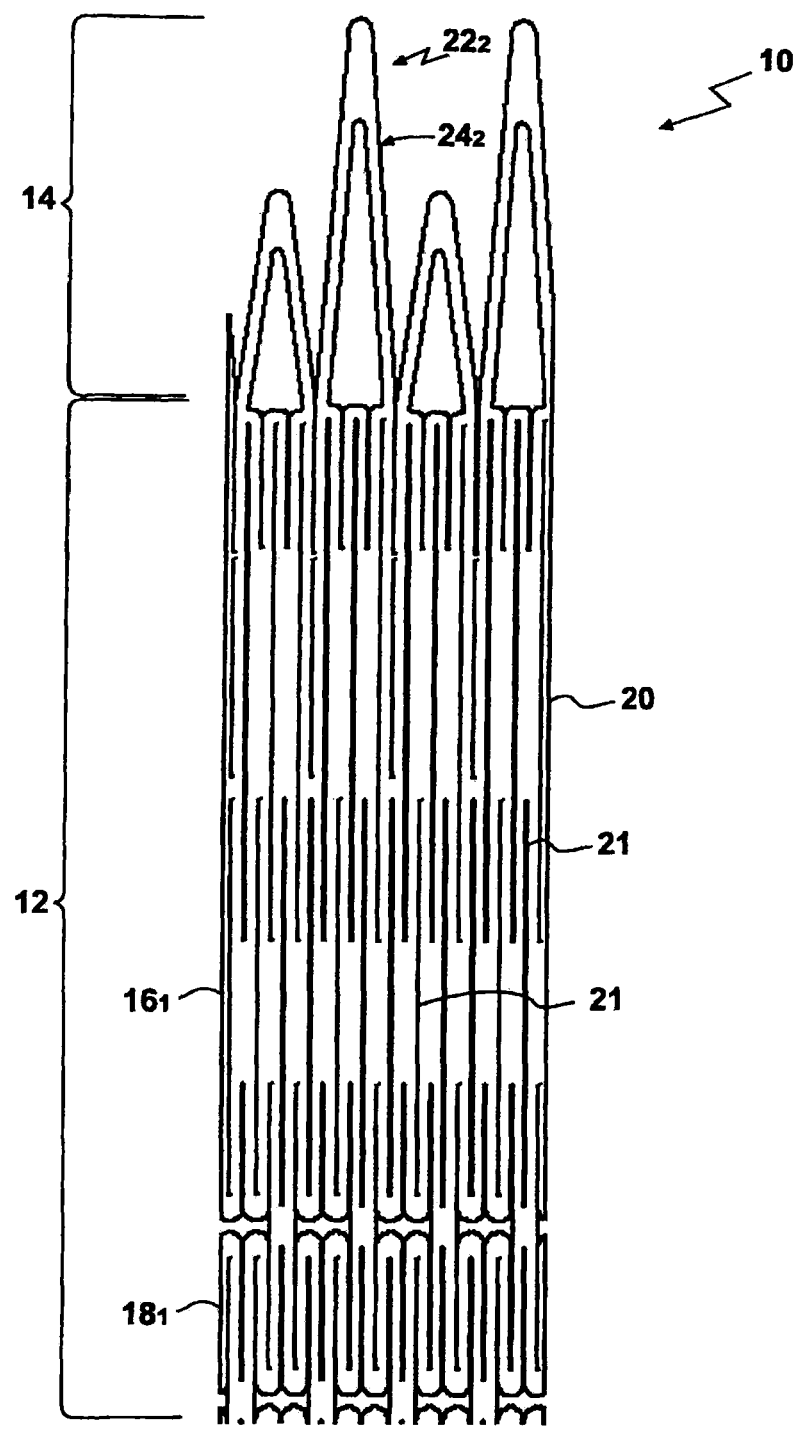
FIG. 2 shows a laser-slotted tube constituting the stent shown in FIG. 1 in an unexpanded configuration, cut longitudinally and flattened.
Figure 3:
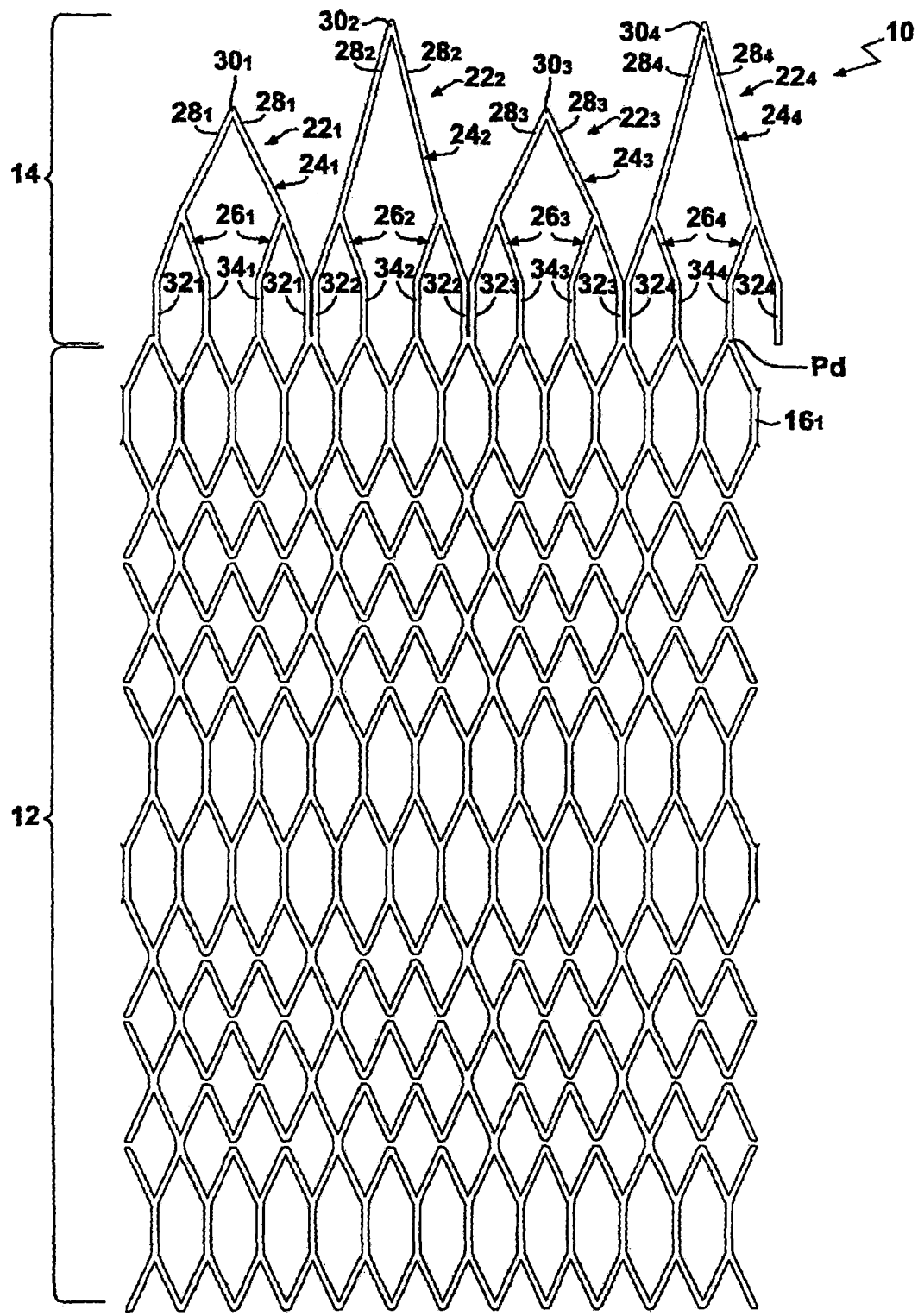
FIG. 3 is a schematic view of the stent shown in FIG. 1 in its expanded configuration, cut longitudinally and flattened.

Referring now to the drawings wherein like reference characters designate like or corresponding parts throughout the several views, a first embodiment of a stent in accordance with the invention, generally designated 10, is illustrated in FIGS. 1-3. Stent 10 comprises two main components: the body 12 and the crown 14 attached to the distal end of the stent body 12. It is understood that crowns may be provided at both ends of the stent body (see FIG. 7). The distal direction is towards the top of the drawing page.

Referring to FIGS. 1 and 3, the stent body 12 is formed of a plurality of interconnected annular closed-cell rings $16_1$, -$16_4$ and Z-rings $18_1$, -$18_6$. Each ring 16, 18 has a plurality, in this case twelve, of distal and proximal peaks Pp, Pd (see rings $16_2$ and $18_1$ in FIG. 1) and longitudinally adjacent rings (except for closed-cell rings $16_2$ and $16_3$) are interconnected at pairs of proximate opposed peaks. Closed-cell rings $16_2$ and $16_3$ are interconnected by shared walls. Generally, a closed-cell ring is formed by a pair of adjacent Z-rings interconnected at every, or at every other, pair of proximate opposed peaks. Reference is made to applicants' U.S. patent application Ser. No. 10/333,600 entitled Multi-Segment Modular Stent and Methods for Manufacturing Stents filed concurrently herewith, and the disclosure of which is incorporated herein in its entirety, with respect to the construction and characteristics of stents made from interconnected closed-cell rings and Z-rings. It is understood that the stent body may be formed with configurations other than shown in the illustrated embodiments.

Referring to FIG. 2, the mesh pattern of stent 10 is cut from a small diameter Nitinol tube 20 by a laser beam 20-80 microns thick. The diameter of Nitinol tube 20 is equal to the diameter of the stent 10 in its completely collapsed state. After cutting appropriate slots 21 in tube 20, the stent has to be gradually expanded to its final diameter, using special mandrels and cycles of annealing or heat treatment in the furnace at high temperatures. Certain designs of mesh patterns may require an additional second round of laser cutting or mechanical disruption after completion of the expansion of the stent.

Referring to FIGS. 1 and 3, the crown 14 of stent 10 is connected to the distal end of stent body 12 and specifically to the distal peaks $P_d$ of the end closed-cell ring $16_1$. Crown 14 comprises four elongated fingers or leaves $22_1$, $22_2$, $22_3$ and $22_4$, each of which is formed by an outer arrowhead-shaped frame $24_1$, $24_2$, $24_3$, $24_4$ and an inner framework $26_1$, $26_2$, $26_3$, $26_4$, respectively. Each outer frame $24_1$-$24_4$ in turn is formed by a pair of main struts $28_1$, $28_1$; $28_2$, $28_2$; $28_3$, $28_3$; $28_4$, $28_4$ that converge in the distal direction and meet at their distal ends at peaks $30_1$, $30_2$, $30_3$, $30_4$, and a pair of base struts $32_1$, $32_1$; $32_2$, $32_2$; $32_3$, $32_3$; $32_4$, $32_4$ that interconnect each pair of main struts 28 of a particular leaf to the distal peaks $P_d$, of closed-cell ring 16. In this embodiment in which closed-cell ring $16_1$ defines twelve distal peaks, and there are four leaves $21_1$-$21_4$, the base struts 32 of each leaf are connected to every third distal peak $P_d$. Each of the inner frameworks $26_1$-$26_4$ comprises a pair of angled support struts $34_1$, $34_1$; $34_2$, $34_2$; $34_3$, $34_3$; $34_4$, $34_4$ each of which has a distal end connected to a respective main strut $28_1$, $28_1$; $28_2$, $28_2$; $28_3$, $28_3$; $28_4$, $28_4$ and a proximal end connected to the distal peak of closed-cell ring $16_1$ adjacent to the peak to which the respective main strut is connected.

The main struts $28_2$, $28_2$ and $28_4$, $28_4$; of leaves $22_2$, $22_4$ are longer than main struts $28_1$, $28_1$ and $28_3$, $28_3$ of leaves $22_1$, $22_3$ and converge at shallower angles so that leaves $22_2$, and $22_4$, which are diametrically opposed to each other, are longer than diametrically opposed leaves $22_1$, $22_3$.

Figure 4A:
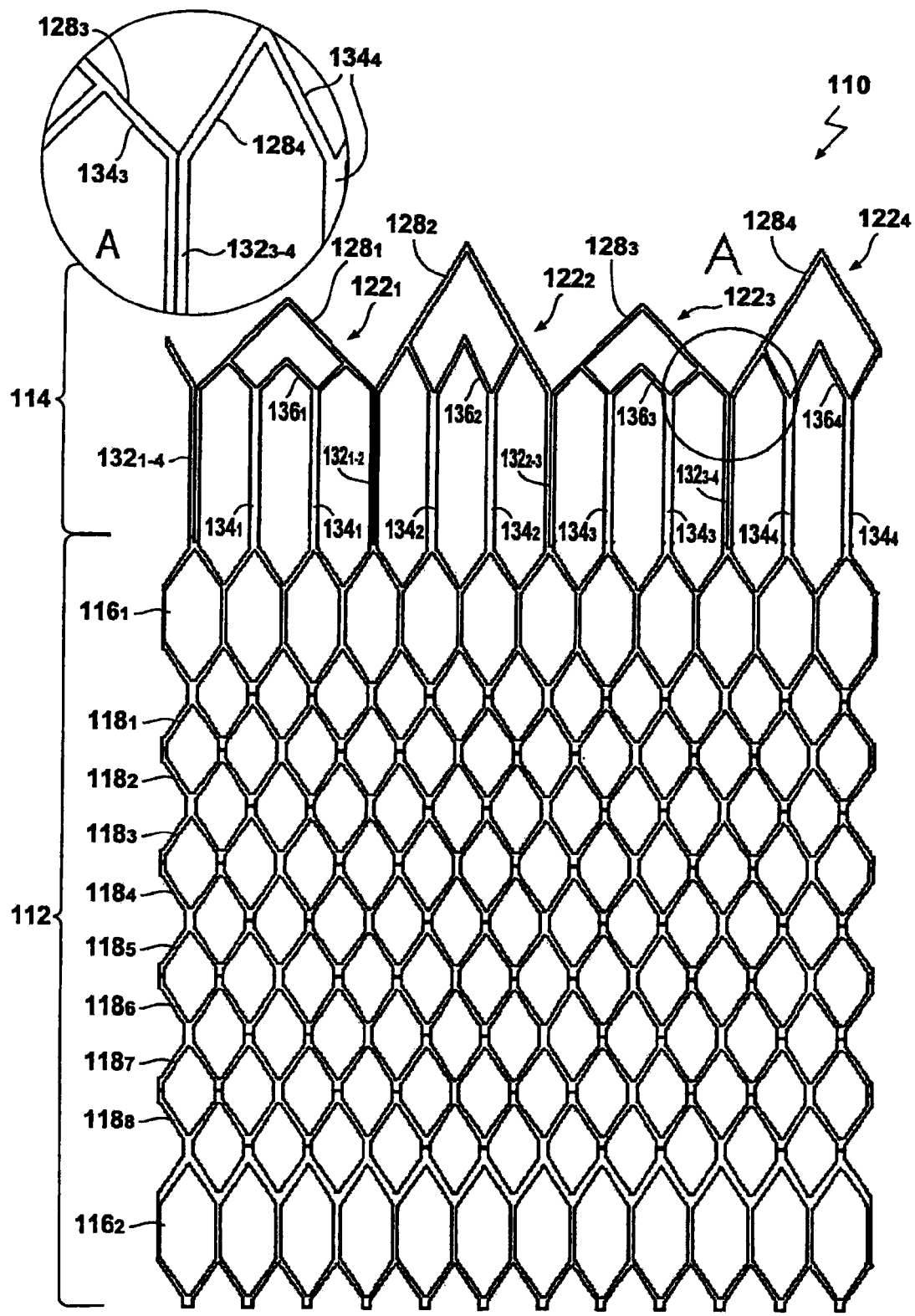
FIG. 4(a) is a schematic perspective view of another embodiment of a stent in accordance with the invention in the process of manufacture, after expansion, but before a second cut.
Figure 4B:
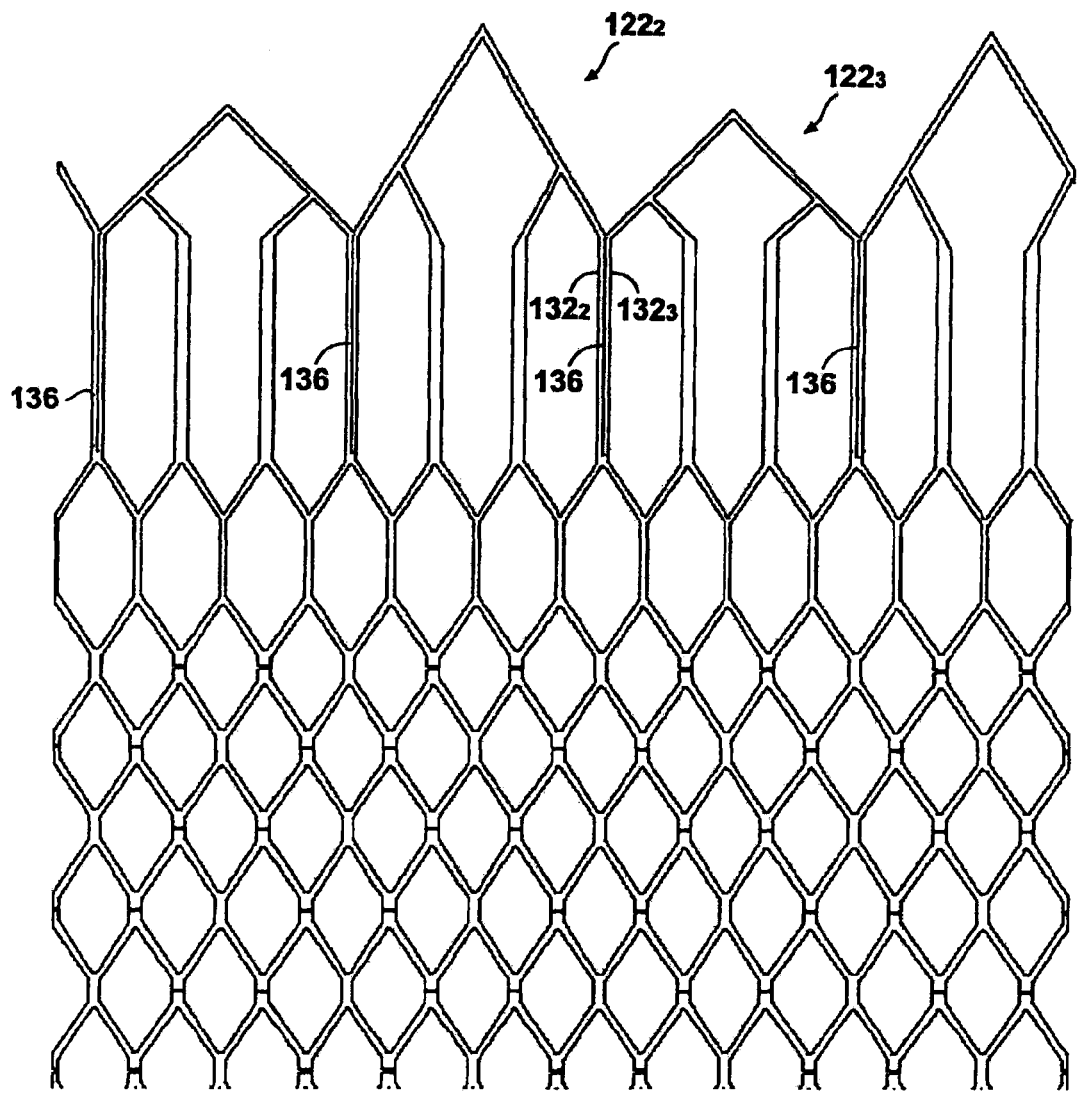
FIG. 4(b) is a schematic perspective view of the stent shown in FIG. 4(a) after a second cut.

Referring to FIGS. 4A and 4B, a stent 110 is illustrated in FIG. 4B which is obtained from a slotted expanded tube 110a shown in FIG. 4A. Stent 110 includes a stent body 112 and a stent crown 114. Stent body 112 includes interconnected closed-cell rings $116_1$ and $116_2$ and Z-rings $118_1$-$118_8$. Stent crown 114, like crown 14 of FIGS. 1-3, includes four leaves $122_1$-$122_4$ including outer arrowhead-shaped frames $124_1$-$124_4$, each of which includes pairs main struts $128_1$, $128_1$; $128_2$, $128_2$; $128_3$, $128_3$; $128_4$, $128_4$.

Stent 110 is shown in FIG. 4A in the process of manufacture. Specifically, a small diameter Nitinol tube has been laser cut and expanded to the configuration shown in FIG. 4A as 110a. This expansion is completed before laser cuts are made to form the base struts 132 of adjacent leaves connected to the same distal peaks $P_d$ of closed-cell ring $116_1$. Thus, during expansion and up to this stage of manufacture, struts $132_{1-2}$, $132_{2-3}$, $132_{3-4}$ and $132_{1-4}$ constitute four unitary structures. Moreover, the inner frameworks $126_1$-$126_4$ are initially formed, and include during expansion and up to the stage of manufacture shown in FIG. 4A, temporary interconnector struts $136_1$-$136_4$ interconnecting respective pairs of angled support struts $134_1$, $134_1$; $134_2$, $134_2$; $134_3$, $134_3$; $134_4$, $134_4$. By maintaining the base struts 132 of adjoining leaves in a unitary form and providing temporary interconnector struts 136 during the expansion and heat treatment of the small diameter tube, the desired shape and geometry of the leaves 122 of crown 114 is achieved uniformly in all four of the crown leaves 122.

Referring to FIG. 4B, when the desired configuration of the crown has been achieved, second laser cuts 136 are made to separate the originally unitary base struts of adjacent leaves, e.g. $132_{2-3}$, (FIG. 4A) into separate base struts $132_2$ and $132_3$ (FIG. 4B), and the temporary struts $136_1$-$136_4$ are removed by laser or manually.

Alternatively, the mesh design of the stent can be laser cut from a large diameter tube, which is equal to the final diameter of a fully expanded stent. This technological process eliminates the need for cycles of expansion and heat treatments. However, these tubes are more expensive and there is a substantial amount of material wasted during the process of laser cutting. Also alternatively, the stent can be constructed from a shape memory wire and laser-welded at certain points to form the desired configuration. The stents are cut is in such manner that the width of the mesh struts is close or equal to the thickness of the wall of the original tube and fine tuned by postproccessing polishing techniques to provide a nearly round configuration in cross section.

The expansive force and the stiffness along the length of the stent can be modulated by changes in the dimensions of the cell geometry (see the attorney docket 471.1007 application). There are no open or sharp edges remaining at either end of the device. This prevents injury to the wall while improving the ability to position, reposition or retrieve the device. Because the struts never overlap, the stent wall thickness is never greater than the wire diameter and both surfaces are smooth. The cells of the stent create an open mesh, which is favorable for maintaining the patency of side branches, and also minimize the length differences between the collapsed and expanded forms of the stent. The shortening of the stent during its expansion depends on the cell geometry, but usually does not exceed 10% of the length of the stent in its completely expanded state. In a preferred embodiment, an intraluminal medical device may include a permanent or temporary implantable stent or stent-graft, a permanent or temporary device impregnated with medications or radioactivity for local therapy.

Figure 5:
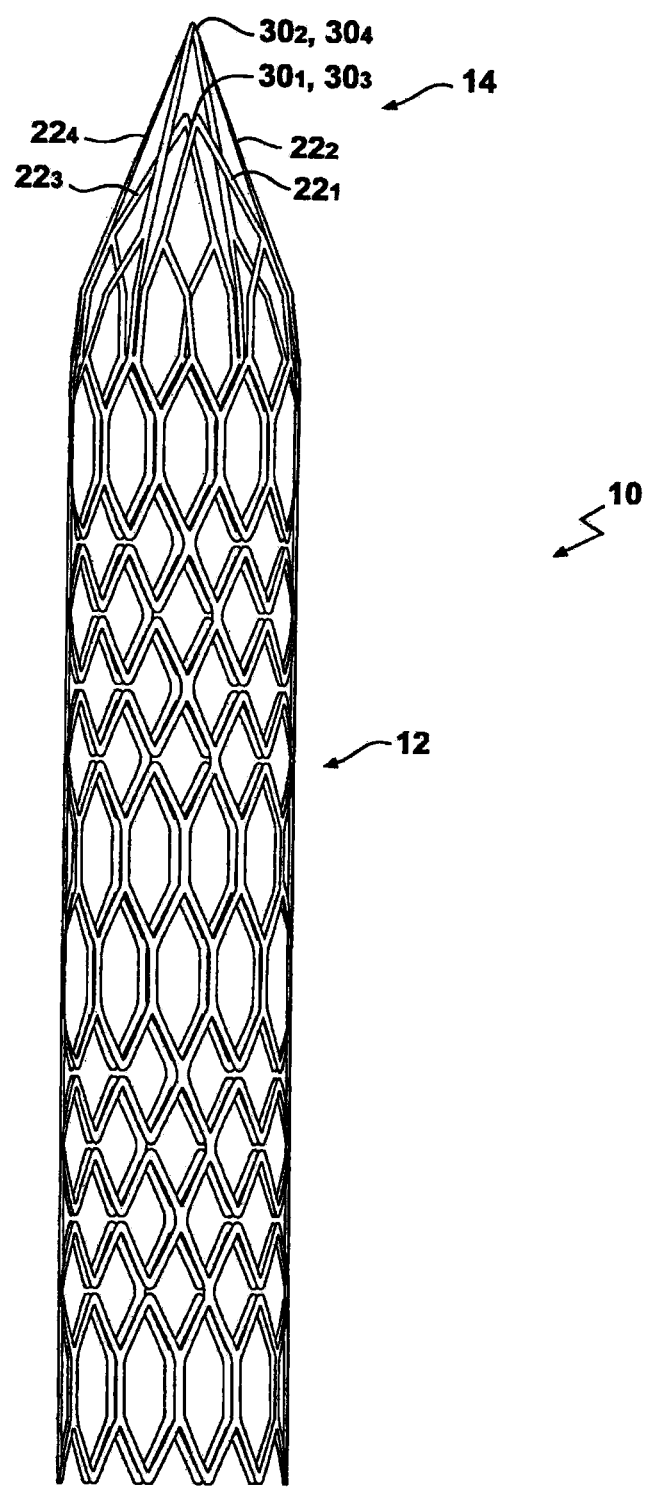
FIG. 5 is a front elevation view of the stent shown in FIG. 1, after cooling with the crown leaves in their collapsed configuration and with a reduction in body diameter of the stent.

In accordance with the invention, the crown is trained to have a second cold shape memory such that after exposure to a certain low temperature, such as by a heat transfer device disclosed in the prior applications, most commonly within the range of −10 C to +35° C., the distal ends of the crown leaves collapse inwardly over the capturing hooks of the retrieval system and serve as anchors by which the entire stent can be reversibly engaged during retrieval and/or repositioning. The leaves, unless restrained by engagement with a retrieval device, undergo a pronounced inward motion until their peaks meet each other at the center of the lumen of the stent. Referring to FIG. 5 which illustrates stent 10 of FIGS. 1-3 after cooling, the opposed pairs of leaves $22_1$, $22_3$; $22_2$, $22_4$ of the crown 14 close together with their respective peaks $30_1$, $30_3$; $30_2$, $30_4$ touching each other at the center of the lumen of the stent. This enables a secure engagement of the capturing hooks of the catheter retrieval system with the stent for its controlled withdrawal from the body or repositioning to another desired location. At the same time, the cooled body 12 of the stent 10 undergoes a reduction in diameter under the two-way memory effect, but to a much lesser extent than the crown leaves. This even minimal collapse of the stent body results in a separation of the stent from the vessel wall and allows stent retrieval or repositioning without causing any trauma to the vessel wall.

A stent having a crown according to the present invention and formed of a shape memory alloy is provided with a two-way memory by training the stent after it has been expanded to its final diameter and all laser-cutting has been completed. It is generally known that to impart a two-way memory to a device formed of a shape memory alloy, the device is subjected to repeated cycles of cooling, deformation and heating (see, e.g. U.S. Pat. No. 5,882,444 to Flomenblit et al.). Here, if the body portion is to be trained first, the expanded tube is cooled to a temperature depending upon the transition temperature of the alloy whereupon the stent is deformed to its collapsed configuration. The stent is allowed to remain in the deformed state for a short period and is then warmed whereupon it returns to its original configuration. This cooling-deformation-heating cycle is repeated until the desired two-way memory is imparted to the stent body. The crown is then trained by subjecting each leaf of the crown to a plurality of cycles including cooling the leaf, "overdeforming" the leaf by bending it inwardly at its base, and then heating the leaf so that it obtains its original configuration. The "overdeformation" is necessary so that the crown leaves will exhibit a greater two-way memory effect than the body portion. For example, for a 10 mm diameter stent, in order to train a crown leaf so that its peak moves radially inwardly a distance of 5 mm into proximity with the peaks of other leaves (see e.g. FIG. 5), during training each leaf should be bent inwardly approximately 180° so that it extends into the lumen of the stent body, during each training cycle. These training cycles are repeated until the enhanced two-way memory effect is imparted to the entire crown.

The leaves of a crown can differ in length as shown in the stent of FIG. 5. By providing that the length of pairs of opposed leaves are different, an unrestricted motion of the leaves of the crown, separate from each other, is facilitated, as the degree of deflection of shorter leaves will be different from the longer leaves. Specifically, shorter leaves $22_1$, $22_3$ demonstrate a more prominent deflection in order for their peaks $30_1$, $30_3$ to meet in the center of the stent lumen (FIG. 5). With this configuration the inward collapse of the shorter leaves does not interfere with the motion of adjacent opposed longer leaves $22_2$, $22_4$, which deflect to a lesser degree (FIG. 50. With this design, during cooling, the peaks of only two opposed leaves (in a four leaf stent design) meet in the center of the stent lumen at one particular spot, which beneficially reduces the amount of metal at the leading end of the stent as it is pulled into the retrieval catheter for stent retrieval and permits the use of smaller diameter receiving sheaths.

Figure 6A:
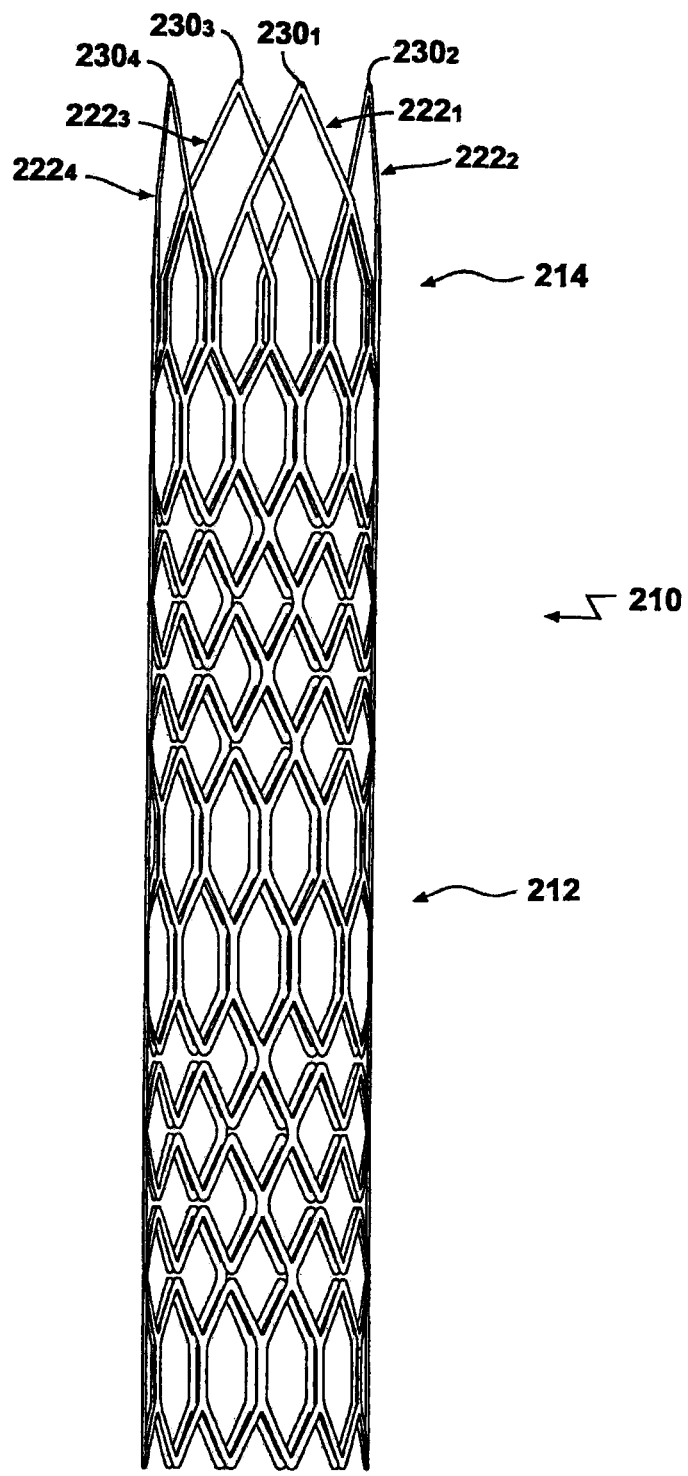
FIG. 6(a) is a front elevation view of another embodiment of a stent in accordance with the invention in its expanded configuration having a crown comprising leaves of equal lengths.
Figure 6B:
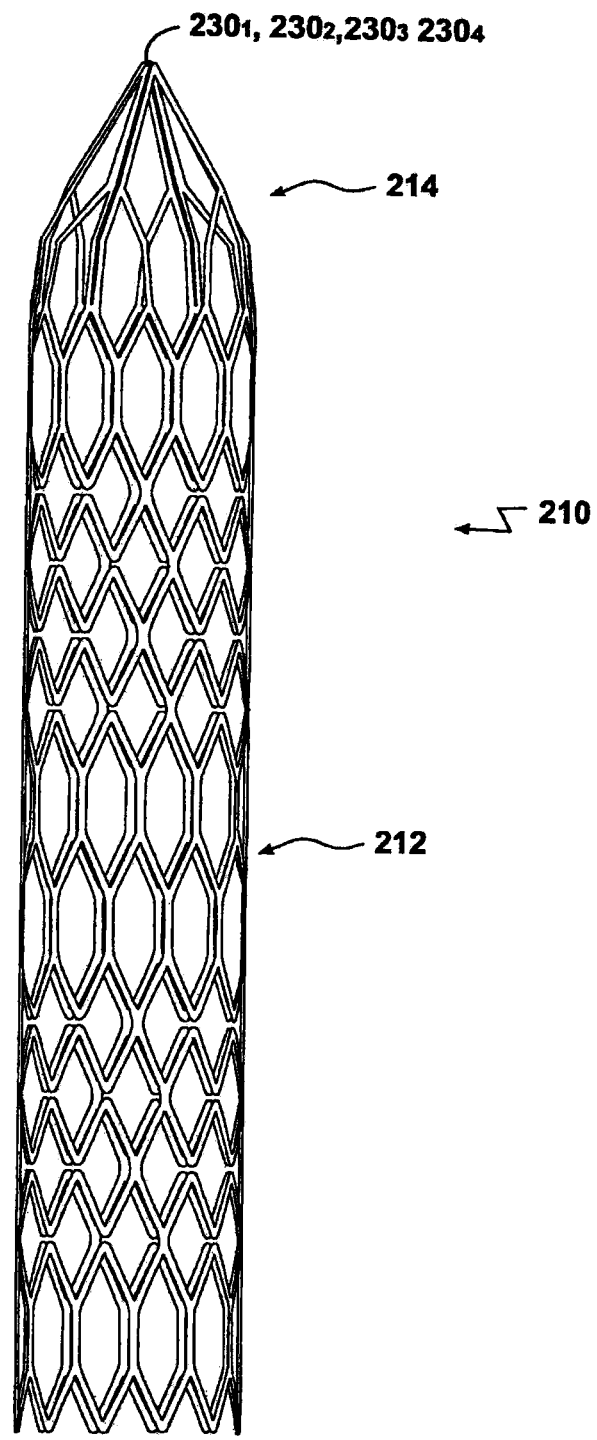
FIG. 6(b) is a front elevation view of the stent shown in FIG. 6(a) after cooling.

As seen in FIG. 6A, the crown 214 of a stent 210 in accordance with the invention can be formed of leaves 222 having the same length. In this case all the leaves of the crown 214 will collapse together and to the same degree so that the peaks 230 of all leaves substantially touch each other at one spot in the center of the lumen of the stent after cooling of the device (FIG. 6B).

Figure 7:
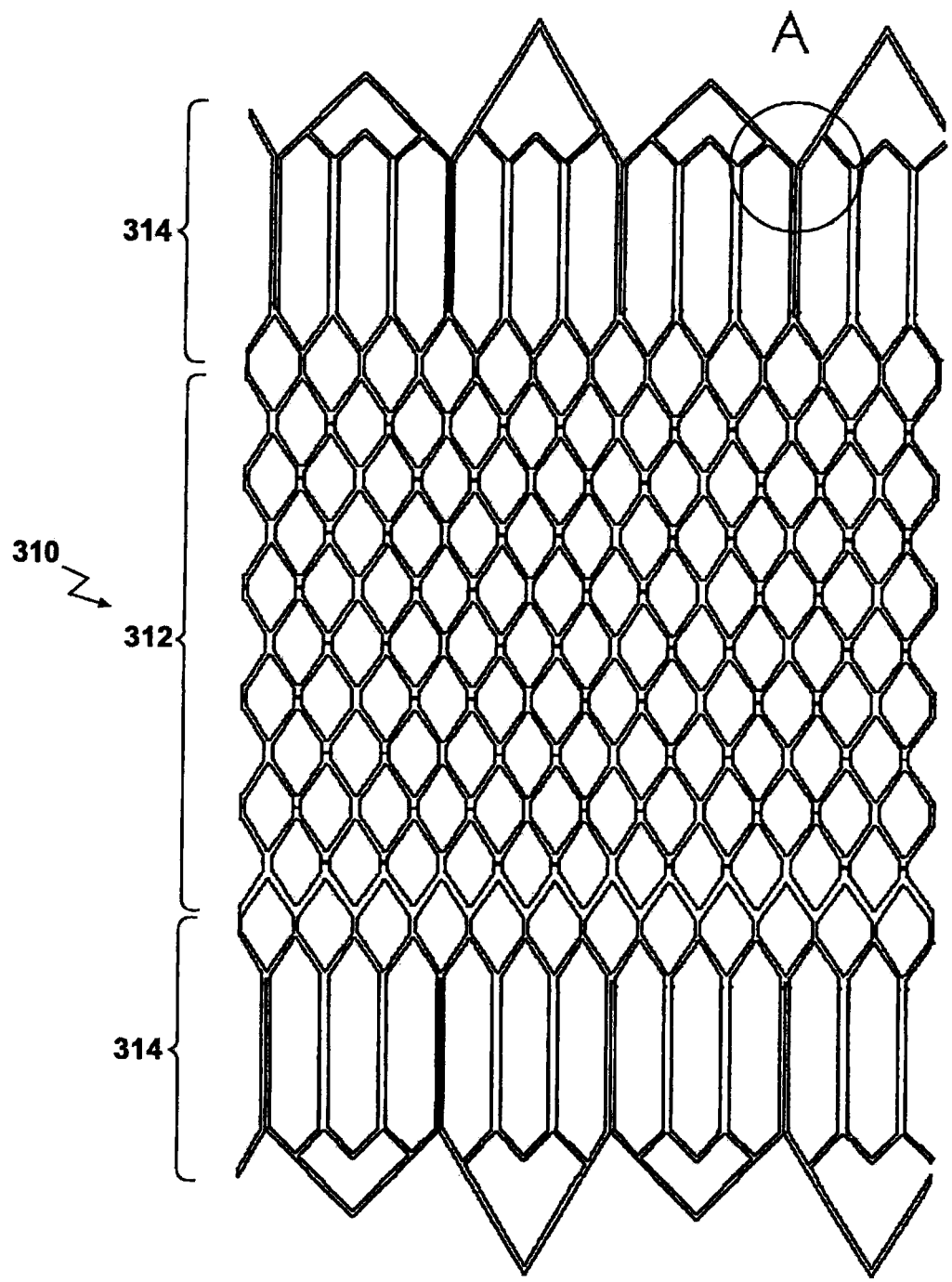
FIG. 7 shows a laser-slotted tube with crowns at each end, cut longitudinally and flattened.

As mentioned above, a crown may be provided at each end of the stent body, such as to eliminate any possibility of the stent being mounted on the delivery catheter with the crown facing in the wrong direction. Depending on the capturing mechanism of the retrieval system, such a stent could be engaged simultaneously at both crowns. An example is illustrated in FIG. 7 which shows a stent 310 having a body 312 and a pair of crowns 314, each attached to one of the ends of the stent body 312.

The geometry, shape and number of the crown leaves can be different and depends on the size of the device, the number of circumferential peaks in the annular ring at the end of the stent body to which the crown is connected, the desired degree of deflection and the construction of the retrievable catheter assembly. The number of peaks in the annular ring of the body of the stent to which the crown is constructed can vary from 4 to 16, and the number of leaves in the stent crown can vary, preferably being from 2 to 8.

For example, in the case where the annular ring at the end of the stent body to which the crown is connected has twelve peaks, the crown can include two, three, four or six leaves, in which case the ends of the outer arrowhead-shaped framework of each leaf is connected to every sixth, fourth, third, or second peak respectively. In the case of a stent body having an end ring defining sixteen peaks, the crown can include two, three, four or eight leaves, in which case the ends of the outer arrowhead-shaped frameworks are connected to every eighth, sixth, fourth, or second peak respectively.

Each outer framework defines a main cell which is longer than the cells of the stent body. Each leaf is generally, although not necessarily, provided with an inner framework connected to the ring peaks intermediate those peaks to which the outer framework is connected. Each inner framework provides support for the outer framework, forms smaller inner cells within each leaf and also serves to eliminate the free intermediate peaks, which otherwise form a serrated edge which might injure the vessel during manipulations with the stent or interfere with the retrieval process.

The outer and inner frameworks together define a plurality of inner cells within each leaf which can be triangular, quadrangular, pentagonal, hexagonal, or some other regular or irregular shape, and which generally are arranged symmetrically within each leaf.

The leaves of a crown are in close proximity to each other but are independent of each other, to provide each leaf with the flexibility required for significant inward motion during retrieval or repositioning. The length of the crown is preferably equal to or greater than the diameter of the stent for optimal collapse under a two way memory effect. For example, the length of the crown of a 10 mm diameter stent would be at least approximately 10 mm, and at least approximately 5 mm long in a stent 5 mm in diameter.

Figure 8A:
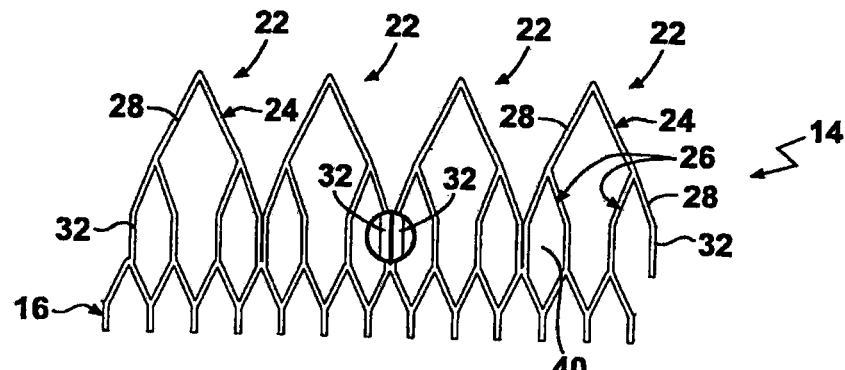
FIGS. 8(a)-8(p) show different embodiments of stent crowns according to the invention.
Figure 8B:
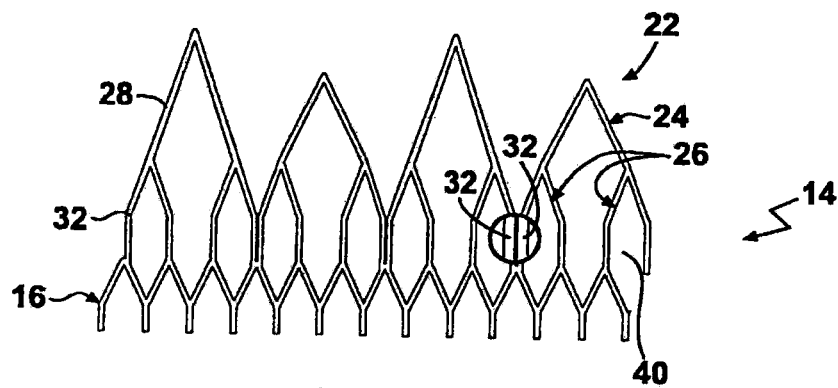
Figure 8C:
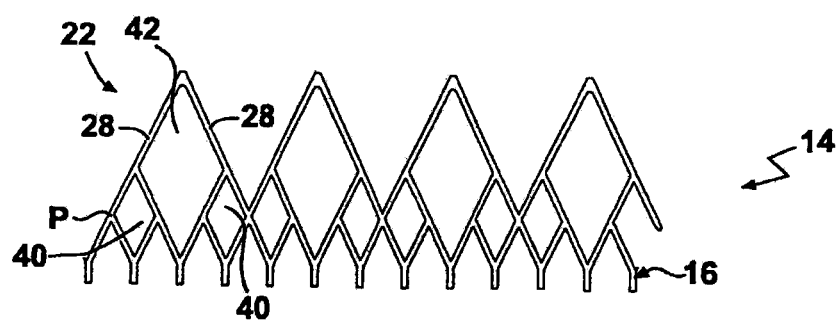
Figure 8D:
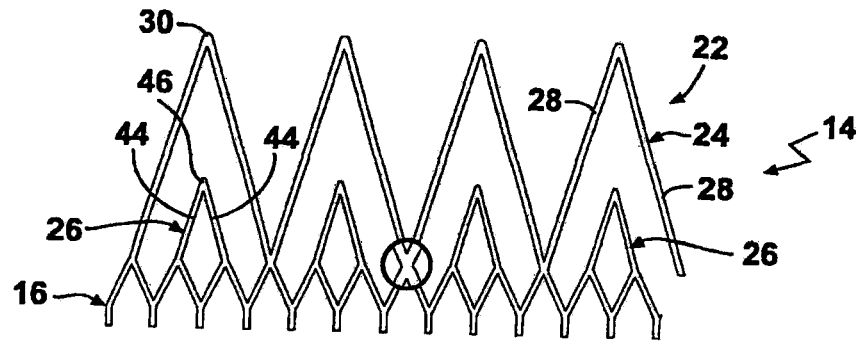
Figure 8E:
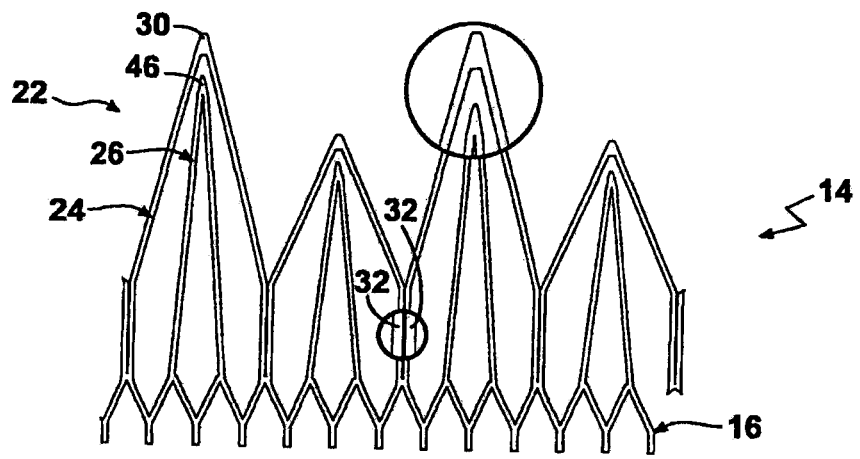
Figure 8F:
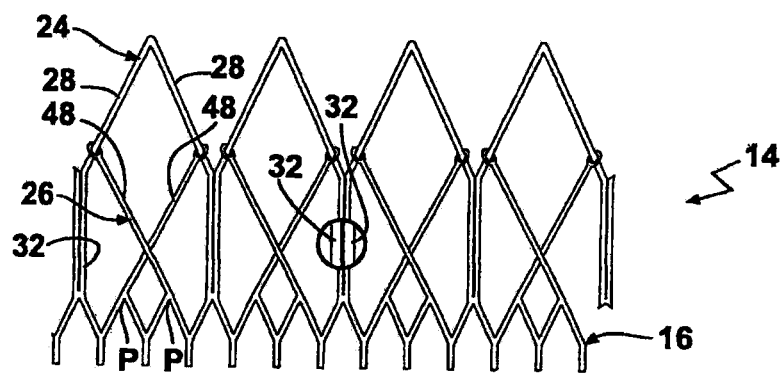
Figure 8G:
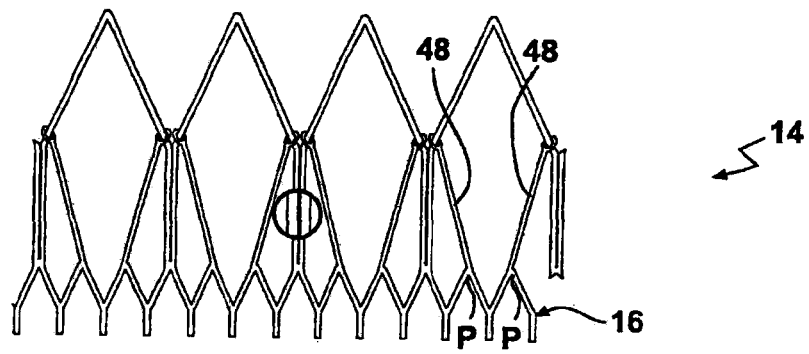
Figure 8H:
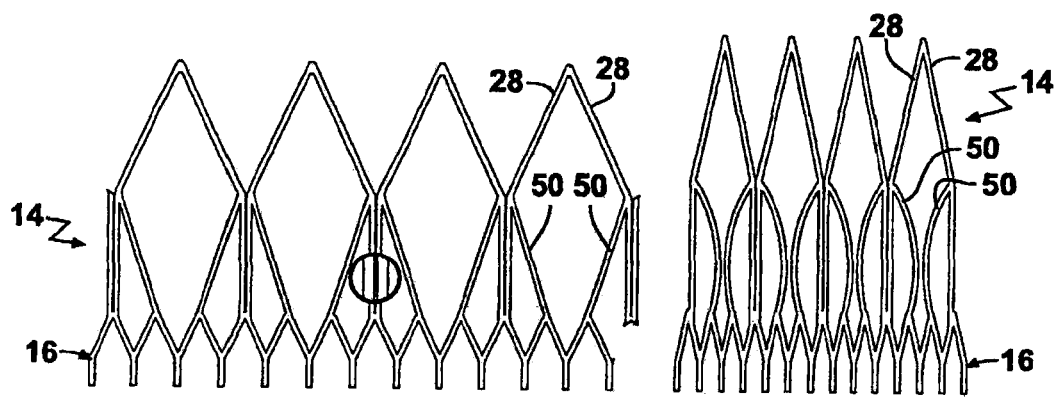
Figure 8I:
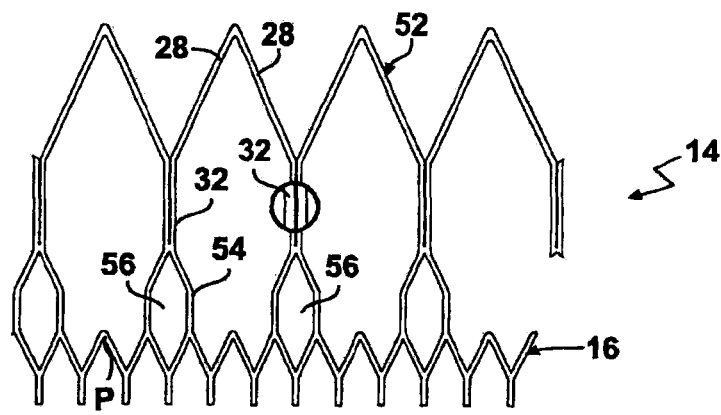
Figure 8J:
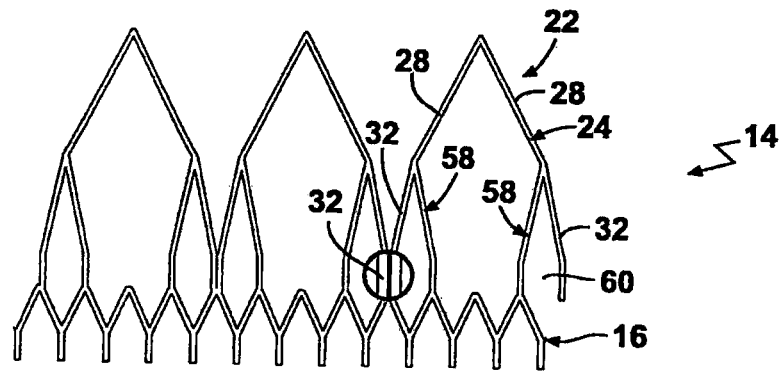
Figure 8K:
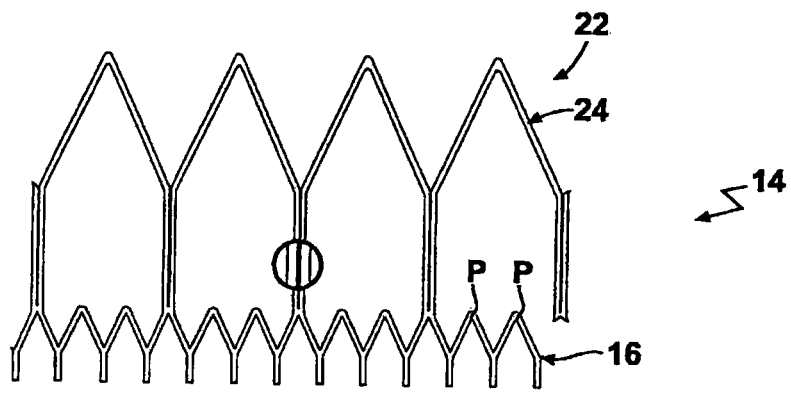
Figure 8L:
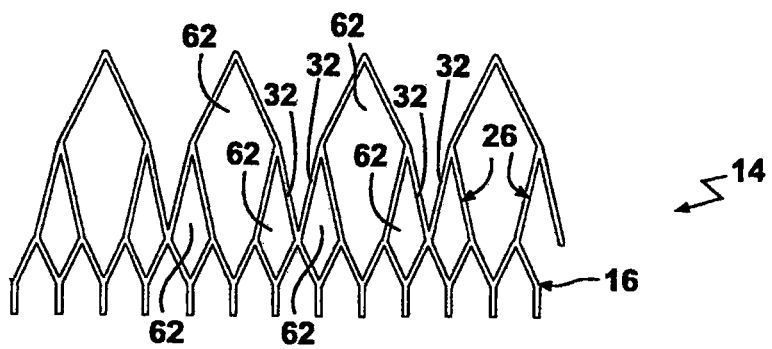
Figure 8M:
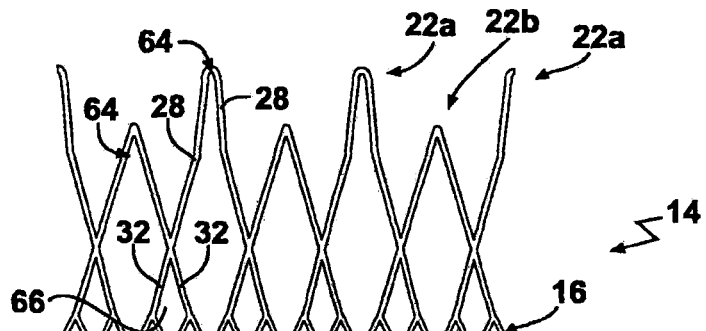
Figure 8N:
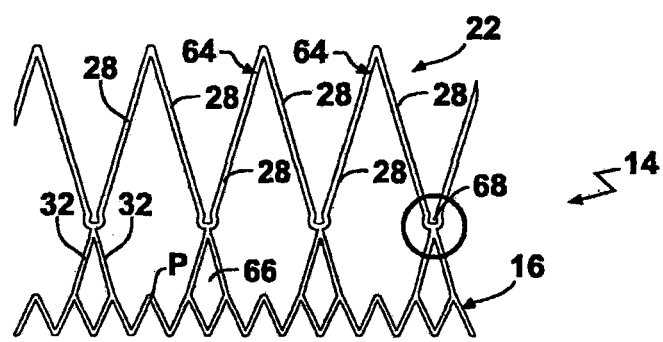
Figure 8O:
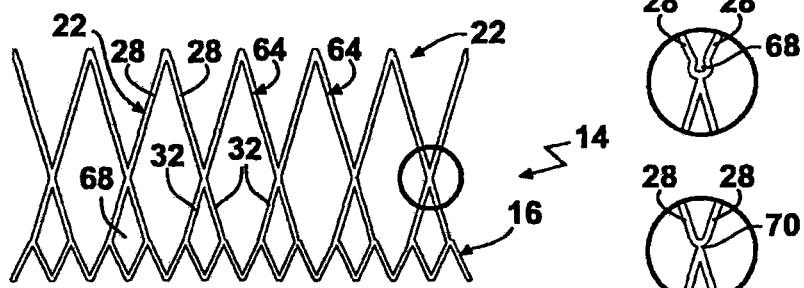
Figure 8O:
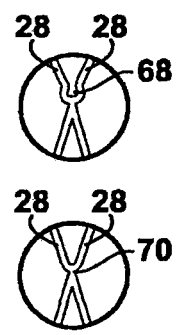
Figure 8P:
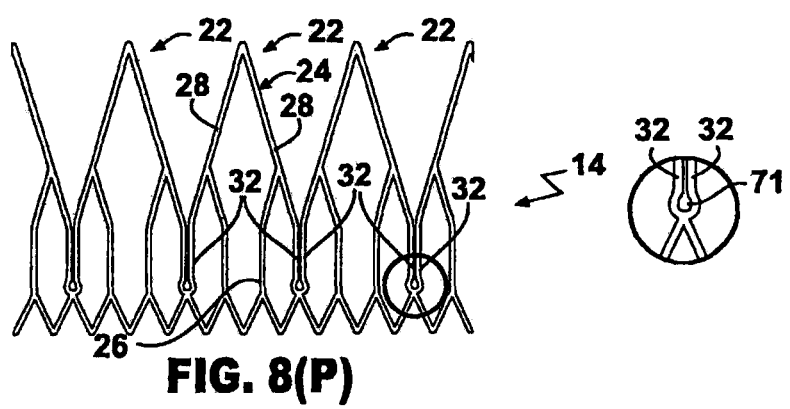
Figure 8P:
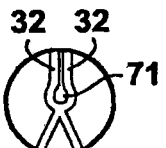

FIGS. 8(a)-8(p) show different configurations of stent crowns 14 connected to the distal annular ring 16 of a stent body. In each case, the annular ring 16 has twelve peaks.

Referring to FIGS. 8(a) and 8(b), the crowns 14, which constitute the crown 214 of FIG. 6 and the crown 14 of FIGS. 1-3 and 5 respectively, include four leaves 22. Each leaf 22 includes an outer, arrowhead-shaped framework 24 and an inner framework 26, and which together define symmetrically arranged inner hexagonal cells 40 within the leaf. A symmetric arrangement provides better geometric functionality, including improved uniformity, during expansion and collapse of the leaves. As pointed out above, these versions are, when made from small-diameter tubes, preferably manufactured using two rounds of laser cutting. The second round of laser cutting, shown at regions S, is performed after the tube has been expanded to its final diameter to achieve the uniformity of the leaf construction and pattern.

Referring to FIG. 8(c), the outer framework 24 of each of the four equal-length leaves 22 is formed of straight main struts 28 that connect directly to every third peak of ring 16, i.e. the base struts 32 in FIGS. 8(a) and 8(b) are eliminated. The frameworks define two symmetric small, quadrilateral cells 40 and a single, central quadrilateral cell 42. The main struts 28 of adjacent leaves that are connected to the same peak of ring 16 diverge immediately from each other at point X so that independent movement of the leaves is assured.

Referring to FIG. 8(d), the outer framework 24 of each of the four equal-length leaves 22 is formed of straight main struts 28 that connect directly to every third peak of ring 16. The inner framework 26 is formed of straight inner struts 44 that connect directly to respective intermediate peaks and meet at an inner peak 46. The inner and outer frameworks 24 and 26 are not directly connected to each other. This eliminates potential geometrical discordance of the outer and inner frameworks during expansion and collapse of the stent.

Referring to FIG. 8(e), the outer framework 24 of each leaf of the two pairs of unequal length leaves 22 is formed in the manner essentially shown in FIG. 8(b) while the inner framework 26 is formed independently of the outer framework 24, in the manner essentially shown in FIG. 8(d). The peaks 46 of the inner frameworks 26 are situated closer to the peaks 30 of the outer frameworks than in the case of FIG. 8(d).

Referring to FIG. 8(f), the outer framework 24 of each of the four equal-length leaves 22 is formed with a pair of main struts 28 and a pair of base struts 32. The inner framework 26 is formed by a pair of crossing wires 48, each wire 48 having one end slidably coupled to a respective main strut 28 and another end connected to the further intermediate peak of annular ring 16. This inner framework 26 is self-adjustable to account for discrepancies in elongation or shortening of inner and outer cells during expansion and collapse of the stent.

Referring to FIG. 8(g), the crown 14 is formed of four equal-length leaves 22 having the same outer frameworks 24 as shown in FIG. 8(f). The inner frameworks 26 differ from those shown in FIG. 2(f) in that the pair of wires 48 do not cross. Rather each wire 48 has one end slidably coupled to a respective main strut 28 and another end connected to the nearer intermediate peak of annular ring 16.

Referring to FIG. 8(h), the crown 14 is formed of four equal-length leaves 22 having the same outer frameworks as shown in FIG. 8(f). Each inner framework 26 includes a strut 50 having one end connected to the outer framework 24 at the intersection of a main strut 28 and associated base strut 32, and its other end connected to a proximate intermediate peak of ring 16. In the collapsed configuration shown in FIG. 8(h), the struts 50 have an arched configuration which become straight when the stent opens.

Referring to FIG. 8(i), the crown 14 is formed of four equal-length leaves 22 formed of arrowhead-shaped single frameworks 52. Each framework 52 includes a pair of converging main struts 28 connected to a pair of base struts 32 which include cell-forming portions 54 which define hexagonal inner cells 56 with the base struts of the adjacent leaf and the space between adjacent peaks of annular ring 16. A central intermediate peak P remains free in this embodiment.

Referring to FIG. 8(j), the crown 14 is formed of three equal length leaves 22. Each leaf 22 comprises an outer arrowhead framework 24 comprising main struts 28 and angled base struts 32 connected to every fourth peak of the twelve-peak end annular ring 16. Each leaf also includes an inner framework 26 comprising a pair of angled inner struts 58, each connected to the corner of a base strut 32 at one end and to the proximate intermediate peak of annular ring 16. The angled base struts 32 and angled inner struts 58 define elongated hexagonal inner cells 60. Only a single central intermediate peak P remains free within each leaf 22.

Referring to FIG. 8(k), the crown 14 is formed of four equal length leaves 22, each leaf 22 including only an outer framework 24 similar to FIG. 8(f). Each of the two intermediate peaks of annular ring 16 remain free.

Referring to FIG. 8(l), the crown 14 is formed of four equal-length leaves 22, each leaf 22 having an outer framework 24 and an inner framework 26. The inner and outer frameworks define a symmetric arrangement of inner cells 62. The outer framework 24 has base struts 32, each of which converges with the base strut 32 of an adjacent outer framework 24 to meet at a single peak. This crown requires only a single round of laser cutting.

Referring to FIG. 8(m), the crown 14 is constituted by six alternating long and short leaves $22_a$, $22_b$, each leaf 22 comprising a single framework 64 defined by a pair of converging main struts 28 which are connected to adjacent peaks of annular ring 16 by diverging base struts 32. The base struts 32 of adjacent frameworks 64 define inner diamond-shaped cells 66 along with annular ring 16. The main struts 28 of the longer leaves $22_a$ are bent to reduce the angle of convergence between them.

Referring to FIG. 8(*n*), the crown 14 is formed of four equal length leaves 22 having a similar construction to FIG. 8(*m*). The leaves differ from FIG. 8(*m*) in that the base struts 32 of the framework 64 of each leaf 22 are connected to every other peak of ring 16, leaving a single free intermediate peak P. Moreover, the adjacent main struts 28 of adjacent frames 64 intersect at an enlarged radius vertex 68 which reduces stress at that region during second way memory inward independent motion of the adjacent leaves.

Referring to FIG. 8(*o*), the crown 14 is formed of six equal length leaves 22 having a similar construction to FIG. 8(*m*). The leaves 22 differ from FIG. 8(*m*) in that the adjacent struts 28 of adjacent leaves 22 intersect at a smooth radius 70 or at a larger radius vertex 68 similar to FIG. 8(*n*).

Referring to FIG. 8(*p*), the crown 14 comprises four equal-length leaves 22 formed of outer frameworks 24 and inner frameworks 26 similar to FIG. 8(*a*), except that the adjacent base struts 32 of adjacent outer frames 24 intersect at an enlarged radius vertex 71 which reduces stress at that region during inward motion of the leaves and promotes better second way memory effect.

The particular construction of the crown may be adapted for a particular configuration of the retrieval/repositioning system used to retrieve and/or reposition the stent. For example, the crowns 14 shown in FIGS. 8(*a*), 8(*b*), 8(*e*), 8(*f*), 8(*g*), 8(*h*), 8(*k*), 8(*n*) and 8(*o*), require at least four capturing hooks spaced around the axis of the catheter, e.g. at equal angles from each other. On the other hand, the stent crown shown in FIG. 8(*j*) requires only three capturing hooks. The stent crowns 14 shown in FIGS. 8(*b*) and 8(*e*) can be used with retrieval systems having capturing hooks of the same or of different lengths.

The crowns of FIGS. 8(*m*) and 8(*o*) need up to seven hooks on the system in order to grasp all the leaves of the crown. It is possible, although not preferable, to capture only longer leaves of the crown shown in FIG. 8(*m*) or every other leaf of the crown shown in FIG. 8(*o*), using 4 capturing hooks on the retrieval system.

For the designs where the leaves of the crown immediately start separating from each other at the peaks of the last annular ring, e.g. the crowns shown in FIGS. 8(*c*), 8(*d*) and 8(*l*), the number of the capturing hooks should correspond to the number of leaves in the crown plus 1, in order to avoid positioning of the hooks in the spaces between the leaves of the crown. With this design when the number of hooks corresponds to the number of leaves and they are equally and evenly spaced from each other, if one hook unintentionally falls into the space between the leaves, all the others also will not engage the crown and the stent will not be retrievable. If at least five hooks are available for four leaves, at least three of them will capture the crown leaves.

Stents with crowns having free intermediate peaks in the end annular ring, such as in FIGS. 8(*i*), 8(*j*), 8(*k*), and 8(*n*) will require a flared receiving sheath for their retrieval in order to make sure that these free peaks do not get caught outside the retrieval catheter.

The crowns described above can be retrieved with a system including a capturing basket formed of capturing hooks covered by a movable outer sheath (similar to what is shown in FIG. 12 and described below), rather than by a frame with hooks coupled to the balloon as shown in the prior applications but it would be more difficult to control the process of capturing and the cooling preferably should be done to a much lower temperature to insure sufficient time to capture the stent before it is warmed up again by the flowing blood.

Figure 9:
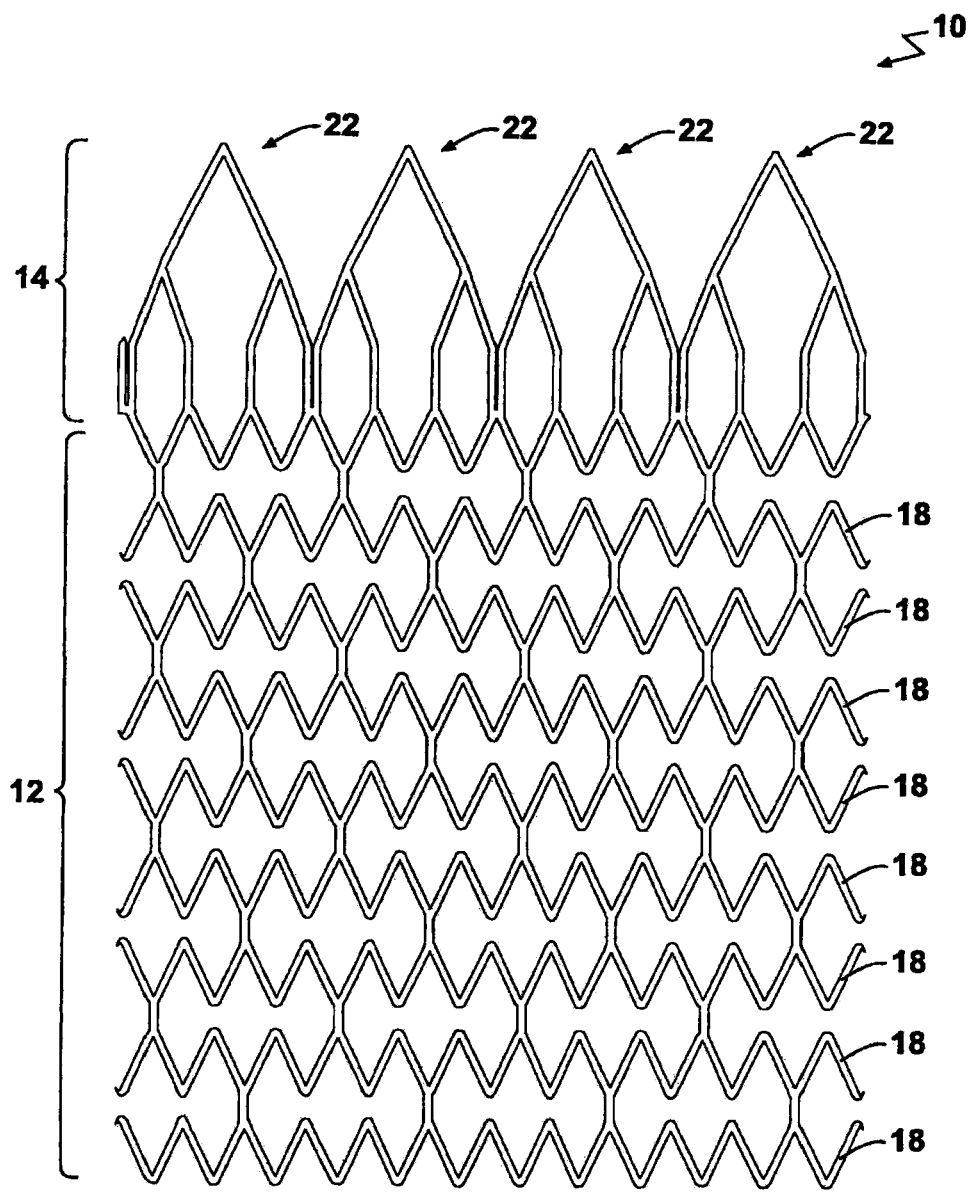
FIG. 9 shows another embodiment of a stent in accordance with the present invention with the body of the stent formed solely of interconnected Z-rings, in an expanded configuration, cut longitudinally and flattened.

The body of a retrievable/repositionable stent of current invention can be of uniform ring design with only Z-rings or only closed-cell rings throughout the entire body of the stent, or constructed from different segments combining alternating Z-rings and closed-cell rings. As mentioned above, and referring to Applicants' application Ser. No. 10/333,600 the design of the body of the stent depends on particular characteristics that have to be achieved for certain clinical applications and on the construction of compatible retrievable systems. For example, referring to FIG. 9, the body 12 of the stent is formed entirely of Z-rings 18 interconnected at every third pair of proximate opposed peaks. On the other hand, this construction may make the process of retrieval more complicated, as there would be so many free peaks of the Z-rings throughout the entire length of the stent, which may interfere with the process of stent retrieval into the sheath. There may also be some stretching of the body of the stent in an accordion fashion during retrieval. The catheter assembly for retrieval of such a stent would have to account for all these drawbacks.

Figure 10:
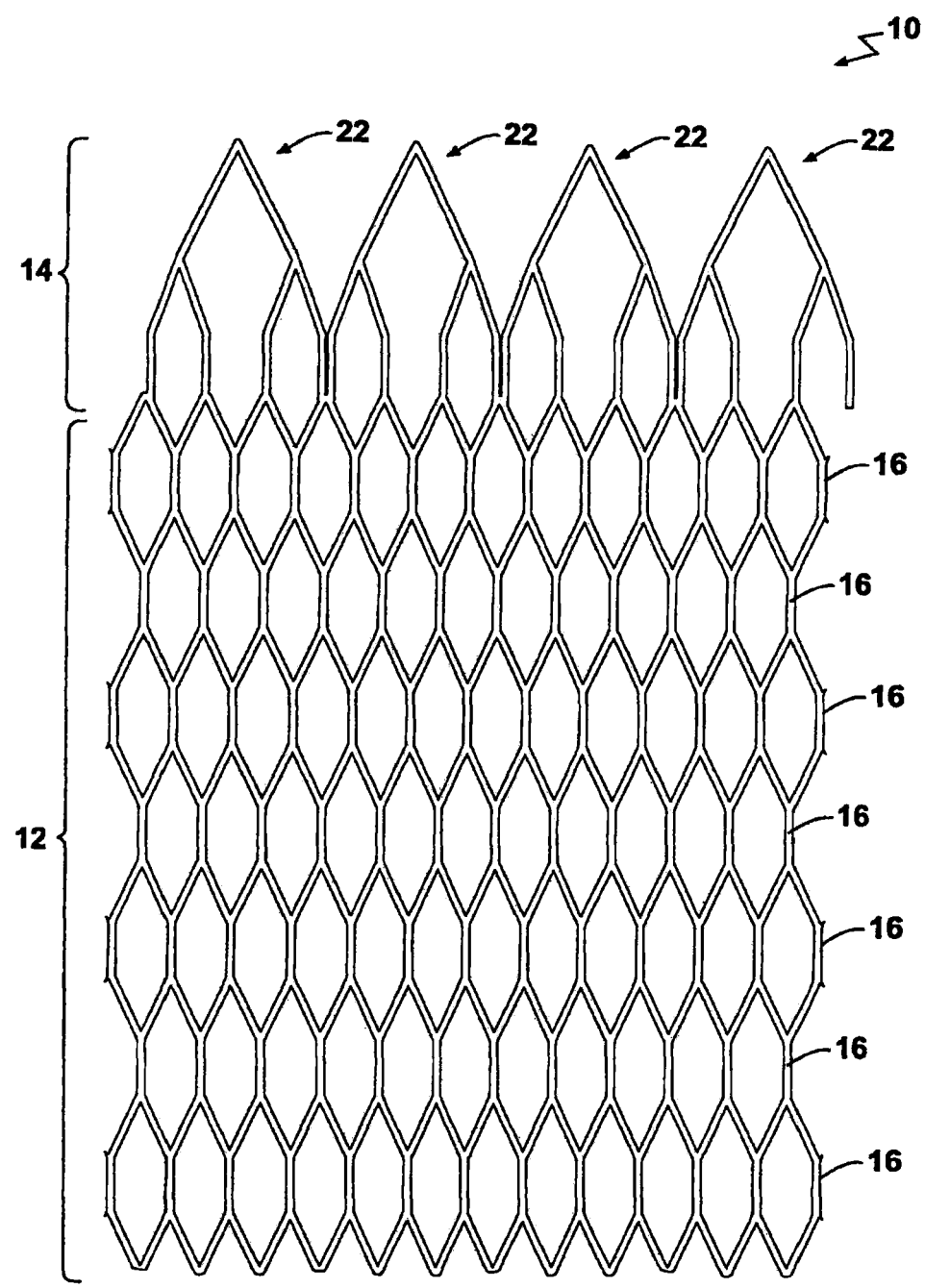
FIG. 10 shows another embodiment of a stent in accordance with the present invention with the body of the stent formed solely of interconnected closed-cell rings, in an expanded configuration, cut longitudinally and flattened.

Referring to FIG. 10, on the other hand, if the stent body 12 is formed entirely of closed-cell rings 16 interconnected by shared walls, the process and the catheter system for stent retrieval can be simplified, but the stent itself would be much less flexible, generally useful for stenting of short straight segments of vessels. Closed-cell ring segments are more prone for better training for second way memory, and exhibit more pronounced reduction in overall diameter during cooling, compared to segments formed of one or more Z-rings. This feature is helpful in the process of stent retrieval. An appropriate combination of alternating segments of Z-rings and closed-cell rings in the body of retrievable/repositionable stents of current invention can provide more optimal stent characteristics for more universal clinical applications.

Figure 11:
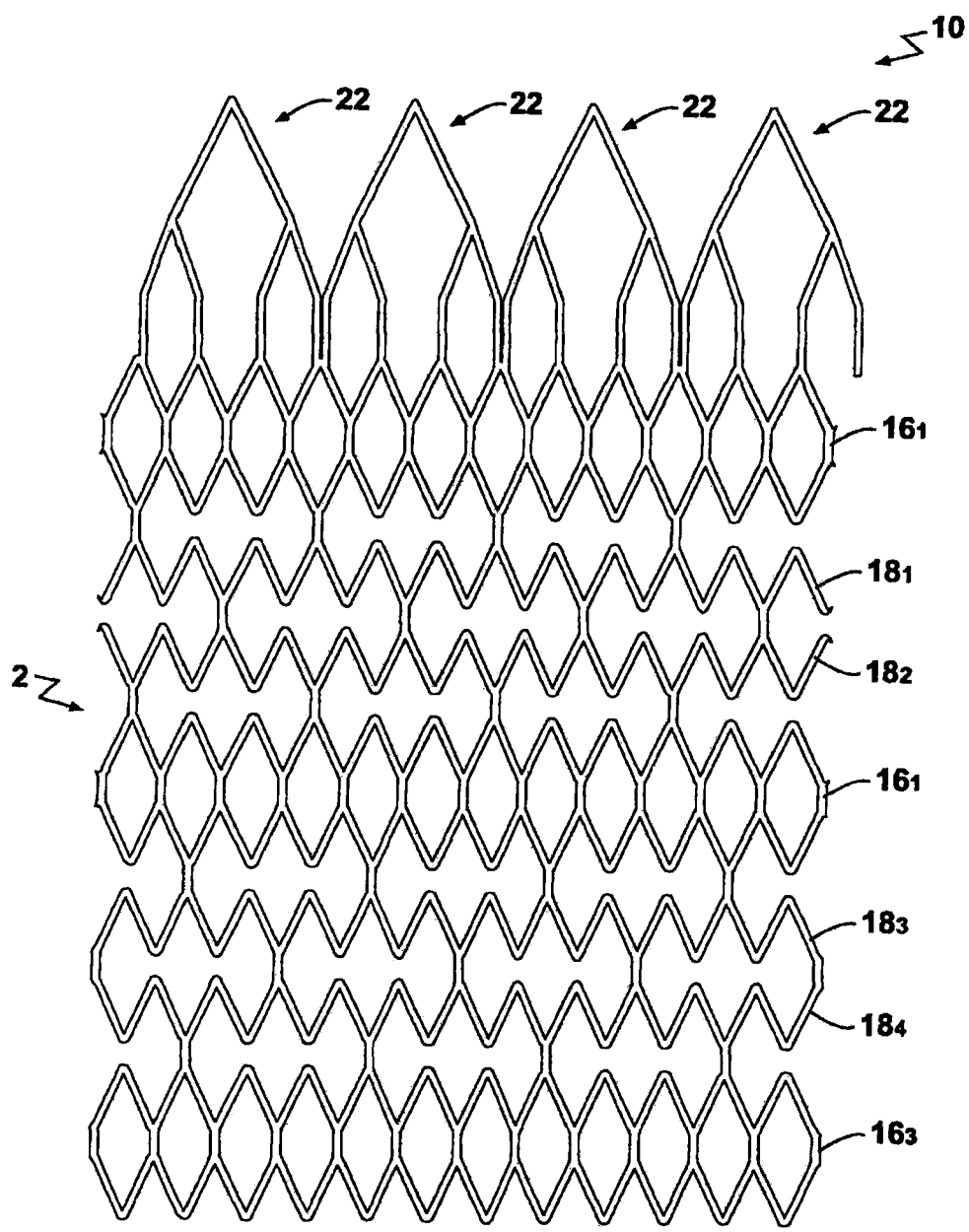
FIG. 11 shows another embodiment of a stent in accordance with the present invention with the body of the stent formed of a combination of interconnected closed-cell rings and Z-rings, in an expanded configuration, cut longitudinally and flattened.

Referring to FIG. 11, a stent 10 illustrated including a body 12 and crown 14. The stent body 12 includes a central segment consisting of a single closed-cell ring $16_2$, a pair of end segments consisting of single closed-cell rings $16_1$ and $16_3$, and a pair of intermediate segments, consisting of pairs of Z-rings $18_1$, $18_2$; $18_3$, $18_4$, situated between the central and respective end closed-cell rings. This design makes the body of the stent more flexible than one having only closed-cell rings, and at the same time reduces the number of free peaks of Z-rings, which facilitates the process of stent retrieval. Segments can consist of one or more closed-cell rings depending on the length of the stent and the desired characteristics. Centrally positioned segments of closed-cell rings exhibit more pronounced second way memory with cooling and help adjacent open cells to reduce more in diameter, causing a smooth transition between the segments.

The segmental/modular construction of stents described in the attorney docket 471.1007 application is applicable to the construction of the body of retrievable/repositionable stents of current invention.

Referring to FIG. 12, a clinical scenario is illustrated in which a stent 10 has been malpositioned inside a vessel 85 only partially covering the area of stenosis (FIG. 12*a*) and it is desired to reposition the stent. In this case, the stent 10 is formed of a two-way shape memory alloy and includes a body 12 and crown 14. In this example, the alloy has a first transition temperature equal to or below body temperature, and a second lower transition temperature in the range of between −10° C. to +35° C. The repositioning system 80, described in detail in the prior applications, includes a balloon 81 mounted on an openable and collapsible frame assembly 83 at the distal end of a catheter. The balloon is covered by a stent-receiving outer sheath 82. Stent-capturing hooks 87 can be opened and closed by manipulation of a stent-capturing sheath 88. A thermal transfer fluid is circulated through the balloon 81 through catheter ports 90 (FIG. 12(*l*)) for heating or cooling the stent. The system is introduced with the balloon 81 in a collapsed state covered by the stent-receiving outer sheath 82 (FIG. 12*b*). The system is positioned so that the collapsed balloon 81 is situated within the lumen of stent 10 that is intended to be retrieved or repositioned. The outer sheath 82 is withdrawn thereby exposing the frame assembly 83 on which the collapsed balloon 81 is mounted (FIG. 12*c*). The frame assembly 83 is then opened (FIG. 12*d*). Expansion of the frame assembly 83 brings the outer wall of balloon 81 into heat transfer relationship with the stent 10. At this time a cold thermal fluid is infused through an inner catheter 84 into the chamber of balloon 81 through ports 90 and the balloon 81 is inflated without creating high internal pressure within it due to an open outflow channel. The diameter of the open wire frame 83 matches the internal diameter of the stent 10 and the cold balloon 81 moves into direct contact with the stent, causing its local cooling to the temperature at or below the second transition temperature, e.g. in the range of −10° C. to 35° C., through the wall forming the balloon 81. The stent becomes soft and pliable at this temperature and reduces at least somewhat in diameter to separate from the wall 86 of vessel 85. The crown 14 shows a greater 2-way memory effect and begins to separate from the vessel wall 86 to a greater extent than the stent body 12 thereby making it easier for the hooks 87 to engage. The next step includes slowly collapsing the wire frame 83 to a smaller diameter by suitably adjusting the catheter assembly while continuing the infusion of cold thermal transfer fluid (FIG. 12(*e*)). The stent crown 14, begins to collapse inwardly and the stent-capturing hooks 87 are advanced over the collapsing crown (FIG. 12(*f*)). This causes secure fixation of the softened cooled stent 10 to the capturing hooks 87 of the catheter repositioning/retrieval assembly 80. The stent is then drawn into the stent-receiving sheath 82 and the infusion of the cold solution/gas into the balloon 81 is terminated (FIG. 12*g*). Collapse of the stent crown prevents migration of the device and slippage over the balloon due to any persistent contact of the stent body with the vessel wall 86, despite the entire stent becoming very soft.

Figure 12A:
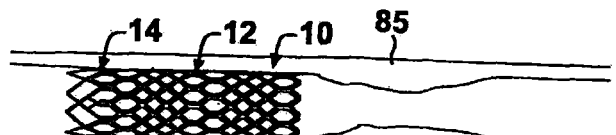
FIGS. 12(a)-12(l) are twelve perspective views showing sequential steps of repositioning an already positioned stent.
Figure 12B:
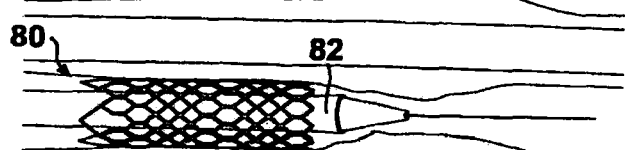
Figure 12C:
Figure 12D:
Figure 12E:
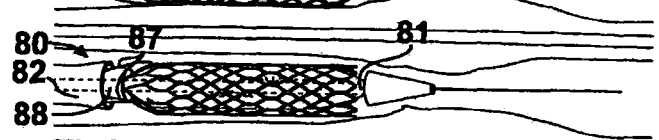
Figure 12F:
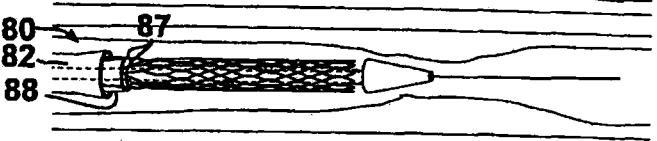
Figure 12G:
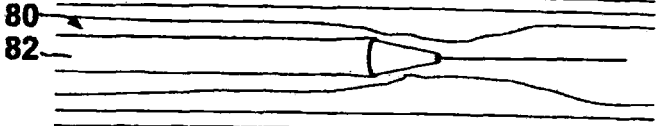
Figure 12H:
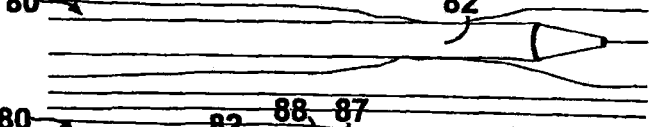
Figure 12I:
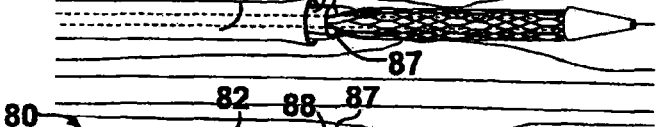
Figure 12J:
Figure 12K:
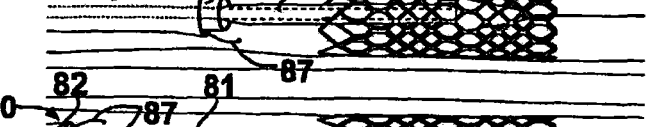
Figure 12L:

The stent can be then completely removed from the body or repositioned while inside the stent-receiving sheath 82 into the proper location (FIG. 12*h*). In this latter case, the stent is then unsheathed (FIG. 12*i*), warms to body temperature and then expands into the original shape and diameter after the stent-capturing hooks are released (FIG. 12*j* and FIG. 12*k*). The reposition and retrieval system 80 is then removed from the body and the repositioned stent remains in place (FIG. 12*l*). Stent retrieval is beneficial in patients where the indication for primary stent placement is an acute intimal dissection, where the stents are used as the vehicle for local delivery of medications or radioactive substances, or in situations when repositioning of a misplaced stent is required.

The same system can be used for retrieval or repositioning of a stent made from a two-way shape memory alloy having a first transition temperature greater than body temperature so that the stent expands to its original shape at a temperature higher than body temperature. These stents require cooling to a temperature below 37° C. in order to exhibit second way memory and partially collapse for safe retrieval, with the other steps of retrieval or repositioning being similar to the ones described in connection with FIG. 12. If repositioning of such a stent is required after it has been recovered into the stent-receiving outer sheath, the position of the closed system is adjusted under direct fluoroscopic guidance. The mounted captured stent is unsheathed and stays in the collapsed state without infusion of a cold solution since the first transition temperature is greater than body temperature. After the stent is precisely positioned at the desired location, the stent-capturing hooks are opened by completely withdrawing the stent-receiving sheath 82. A warm solution is infused into the balloon chamber and the frame 83 is opened. The stent expands to its final diameter and after the holding mechanism is released, the system can be withdrawn, with the stent remaining in place at the desired location.

All currently available stents can be modified, trained or supplied with a special crown attachment, exhibiting the second way memory and can be retrieved from the body or repositioned into the desired location using minimally invasive endoluminal techniques.

Obviously, numerous variations of the present invention are possible within the scope of the claims appended hereto. Accordingly, the invention may be practiced otherwise than as specifically described herein.

We claim:

1. An expandable stent formed of a shape memory material comprising:
   an elongated tubular body; and
   at least one crown connected to a respective longitudinal end of said body, said crown including a plurality of unconnected arrowhead-shaped leaves, each leaf having a longitudinally extending outer frame which is separate from and unconnected to the outer frame of any of the other leaves, each outer frame further having a first end connected to said end of said body and a second free end, and wherein each leaf includes said outer frame and an inner frame situated within said outer frame, wherein said stent body comprises an annular ring constituting said end of said stent body to which said crown is connected, said annular ring defining a plurality of adjacent peaks situated around the circumference of said end of said stent body; and wherein said outer frame of each leaf includes two struts directly connected at one of their ends to a pair of non-adjacent peaks of said end annular ring, and wherein said inner frame of each leaf includes two struts directly connected at one of their ends to respective intermediate peaks situated between said non-adjacent peaks of said end annular ring, wherein said stent material is trained to exhibit two-way shape memory properties such that when the stent is cooled in a predetermined temperature range, said free ends of said leaves move radially inwardly into proximity with each other, wherein the plurality of leaves are trained to have greater two-way shape memory effect than the elongated tubular body, and wherein said stent body comprises a plurality of interconnected closed-cell rings and Z-rings, and the end ring of said stent body to which said crown is connected comprises a closed-cell ring.

2. A stent as recited in claim 1 wherein said stent includes a pair of crowns, each crown connected to a respective end of said stent body.

3. A stent as recited in claim 1 wherein said leaf comprises a single arrowhead-shaped frame.

4. A stent as recited in claim 1 wherein the lengths of all of said leaves of said crown are substantially the same.

5. A stent as recited in claim 1 wherein said leaves of said crown have different lengths.

6. A stent as recited in claim 1 wherein said plurality of leaves includes from two to eight leaves.

7. A stent as recited in claim 1 wherein said crown includes a plurality of pairs of equal-length leaves situated at diametrically opposed regions of said stent body end to which said crown is connected.

8. A stent as recited in claim 7 wherein the leaves of each of said pairs have the same length which is different from the length of the leaves of other pairs of leaves.

9. A stent as recited in claim 8 wherein said crown comprises two pairs of diametrically opposed leaves.

10. A stent as recited in claim 1 wherein each frame of each leaf includes a plurality of struts, two of said struts converging at one of their ends to form a peak.

11. A stent as recited in claim 1 wherein said two struts of each outer frame are connected to adjacent peaks of said annular ring.

12. A stent as recited in claim 1 wherein said two struts of each outer frame are connected a pair of peaks of said annular ring which are separated from each other by a single intermediate peak.

13. A stent as recited in claim 1 wherein said two struts of each outer frame are connected to a pair of peaks of said annular ring which are separated from each other by two intermediate peaks.

14. A stent as recited in claim 1 wherein said two struts of each frame are connected to a pair of peaks of said annular ring which are separated from each other by three intermediate peaks.

15. A stent as recited in claim 1 wherein said outer and inner frames of each leaf define a plurality of inner cells.

16. A stent as recited in claim 15 wherein said inner cells of each leaf are symmetrically arranged.

17. A stent as recited in claim 1 wherein said outer and inner frames of each leaf are connected to each other.

18. A stent as recited in claim 1 wherein said outer and inner frames of each leaf are unconnected to each other.

19. A stent as recited in claim 1 wherein said outer and inner frames of each leaf define a plurality of inner cells.

20. A stent as recited in claim 1 wherein said outer frame of each leaf includes a pair of base struts connected to the end of said body and a pair of main struts connected to said base struts and converging to form a peak.

21. A stent as recited in claim 1 wherein said stent body comprises a central segment formed of at least one closed-cell ring and a pair of segments adjacent to said central segment formed of at least one Z-ring.

22. A stent as recited in claim 21 wherein said stent body comprises a pair of end segments formed of at least one closed-cell ring.

23. A stent as recited in claim 1 wherein said stent is formed of Nitinol.

24. An expandable stent formed of a shape memory material comprising:
   an elongated tubular body comprising a plurality of interconnected cells having longitudinal dimensions; and
   at least one crown connected to a respective longitudinal end of said body, said crown including a plurality of unconnected arrowhead-shaped leaves, each leaf having a longitudinally extending outer frame which is separate from and unconnected to the outer frame of any of the other leaves, each outer frame further having a first end connected to said end of said body and a second free end, and wherein each leaf includes said outer frame and an inner frame situated within said outer frame, wherein said stent body comprises an annular ring constituting said end of said stent body to which said crown is connected, said annular ring defining a plurality of adjacent peaks situated around the circumference of said end of said stent body; and wherein said outer frame of each leaf includes two struts directly connected at one of their ends to a pair of non-adjacent peaks of said end annular ring, and wherein said inner frame of each leaf includes two struts directly connected at one of their ends to respective intermediate peaks situated between said non-adjacent peaks of said end annular ring, wherein said stent material is trained to exhibit two-way shape memory properties such that when the stent is cooled in a predetermined temperature range, said free ends of said leaves move radially inwardly into proximity with each other, wherein the plurality of leaves are trained to have greater two-way shape memory effect than the elongated tubular body, wherein said stent body comprises a plurality of interconnected closed-cell rings and Z-rings, and the end ring of said stent body to which said crown is connected comprises a closed-cell ring; and wherein said leaves of said crown have longitudinal dimensions greater than the longitudinal dimensions of the cells of said stent body.

25. An expandable stent formed of a shape memory material comprising:
   an elongated tubular body having a certain diameter in its expanded condition; and
   at least one crown connected to a respective longitudinal end of said body, said crown including a plurality of unconnected arrowhead-shaped leaves, each leaf having a longitudinally extending outer frame which is separate from and unconnected to the outer frame of any of the other leaves, each outer frame further having a first end connected to said end of said body and a second free end, and wherein each leaf includes said outer frame and an inner frame situated within said outer frame, wherein said stent body comprises an annular ring constituting said end of said stent body to which said crown is connected, said annular ring defining a plurality of adjacent peaks situated around the circumference of said end of said stent body; and wherein said outer frame of each leaf includes two struts directly connected at one of their ends to a pair of non-adjacent peaks of said end annular ring, and wherein said inner frame of each leaf includes two struts directly connected at one of their ends to respective intermediate peaks situated between said non-adjacent peaks of said end annular ring, wherein said stent material is trained to exhibit two-way shape memory properties such that when the stent is cooled in a predetermined temperature range, said free ends of said leaves move radially inwardly into proximity with each other, wherein the plurality of leaves are trained to have greater two-way shape memory effect than the elongated tubular body, wherein said stent body comprises a plurality of interconnected closed-cell rings and Z-rings, and the end ring of said stent body to which said crown is connected comprises a closed-cell ring; and wherein said leaves of said crown have longitudinal dimensions about equal to or greater than said diameter of said tubular body.

* * * * *